(12) United States Patent
Lorio

(10) Patent No.: US 11,857,429 B2
(45) Date of Patent: Jan. 2, 2024

(54) INTERVERTEBRAL CAGE APPARATUS AND SYSTEM AND METHODS OF USING THE SAME

(71) Applicant: EIT Emerging Implant Technologies GmbH, Wurmlingen (DE)

(72) Inventor: Morgan Packard Lorio, Nashville, TN (US)

(73) Assignee: EIT Emerging Implant Technologies GmbH

( * ) Notice: Subject to any disclaimer, the term of this patent is extended or adjusted under 35 U.S.C. 154(b) by 938 days.

(21) Appl. No.: 16/732,428

(22) Filed: Jan. 2, 2020

(65) Prior Publication Data

US 2020/0138588 A1 May 7, 2020

Related U.S. Application Data

(62) Division of application No. 14/422,750, filed as application No. PCT/US2013/056500 on Aug. 23, 2013, now Pat. No. 10,568,745.

(Continued)

(51) Int. Cl.
*A61F 2/44* (2006.01)
*A61F 2/46* (2006.01)
(Continued)

(52) U.S. Cl.
CPC .............. *A61F 2/442* (2013.01); *A61F 2/447* (2013.01); *A61F 2/4611* (2013.01);
(Continued)

(58) Field of Classification Search
None
See application file for complete search history.

(56) References Cited

U.S. PATENT DOCUMENTS

| 5,549,679 A | 8/1996 | Kuslich |
| 5,571,189 A | 11/1996 | Kuslich |

(Continued)

FOREIGN PATENT DOCUMENTS

| CN | 101031259 A | 9/2007 |
| JP | 2003-505149 A | 2/2003 |

(Continued)

OTHER PUBLICATIONS

International Search Report and Written Opinion in Application No. PCT/US2013/056500, dated Dec. 6, 2013 in 15 pages.

*Primary Examiner* — Sameh R Boles
(74) *Attorney, Agent, or Firm* — BakerHostetler

(57) ABSTRACT

An intervertebral cage and intervertebral cage apparatus and a method for using the intervertebral cage and/or the intervertebral cage apparatus. The intervertebral cage can be any desired material including a memory material. The intervertebral cage apparatus can include the intervertebral cage and one or both of a variable volume pouch and a deployment cable. The variable volume pouch can be inserted into an internal volume of the intervertebral cage and affixed to the intervertebral cage. The variable volume pouch can be filled with material to achieve an expanded state. The variable volume pouch can assist in the deployment of the intervertebral cage. The deployment cable can be attached to the intervertebral cage and can include features to facilitate that attachment. The deployment cable can apply a force to the intervertebral cage to deploy the intervertebral cage, and can include features to lock the (Continued)

intervertebral cage in the deployed configuration. An implantation tool can be used to apply force to the intervertebral cage to deploy the intervertebral cage.

12 Claims, 26 Drawing Sheets

Related U.S. Application Data

(60) Provisional application No. 61/778,271, filed on Mar. 12, 2013, provisional application No. 61/693,738, filed on Aug. 27, 2012.

(51) Int. Cl.
*A61F 2/30* (2006.01)
*A61F 2/28* (2006.01)

(52) U.S. Cl.
CPC ..... *A61F 2/4601* (2013.01); *A61F 2002/2835* (2013.01); *A61F 2002/305* (2013.01); *A61F 2002/30019* (2013.01); *A61F 2002/3055* (2013.01); *A61F 2002/30092* (2013.01); *A61F 2002/30143* (2013.01); *A61F 2002/30331* (2013.01); *A61F 2002/30359* (2013.01); *A61F 2002/30448* (2013.01); *A61F 2002/30462* (2013.01); *A61F 2002/30467* (2013.01); *A61F 2002/30471* (2013.01); *A61F 2002/30545* (2013.01); *A61F 2002/30556* (2013.01); *A61F 2002/30579* (2013.01); *A61F 2002/30581* (2013.01); *A61F 2002/30584* (2013.01); *A61F 2002/30588* (2013.01); *A61F 2002/30593* (2013.01); *A61F 2002/30594* (2013.01); *A61F 2002/30774* (2013.01); *A61F 2002/30785* (2013.01); *A61F 2002/30789* (2013.01); *A61F 2002/30828* (2013.01); *A61F 2002/4415* (2013.01); *A61F 2002/4627* (2013.01); *A61F 2310/00011* (2013.01)

(56) References Cited

U.S. PATENT DOCUMENTS

| | | | |
|---|---|---|---|
| 6,039,761 | A | 3/2000 | Li et al. |
| 6,656,178 | B1 | 12/2003 | Gerrit et al. |
| 7,445,636 | B2 | 11/2008 | Michelson |
| 7,513,900 | B2 | 4/2009 | Carrison et al. |
| 7,621,950 | B1 | 11/2009 | Globerman et al. |
| 2005/0070911 | A1 | 3/2005 | Carrison et al. |
| 2008/0015701 | A1 | 1/2008 | Garcia et al. |
| 2008/0243255 | A1 | 10/2008 | Butler et al. |
| 2009/0270873 | A1* | 10/2009 | Fabian ............ A61F 2/442 606/205 |
| 2012/0083887 | A1* | 4/2012 | Purcell ............ A61F 2/4601 623/17.16 |
| 2012/0083889 | A1 | 4/2012 | Purcell et al. |
| 2012/0123546 | A1* | 5/2012 | Medina ............ A61F 2/447 623/17.16 |

FOREIGN PATENT DOCUMENTS

| | | |
|---|---|---|
| JP | 2003-526458 A | 9/2003 |
| WO | 01/68005 A2 | 9/2001 |
| WO | 2007/076377 A2 | 7/2007 |
| WO | 2008/152501 A2 | 12/2008 |
| WO | 2009/125242 A1 | 10/2009 |
| WO | 2012/007918 A2 | 1/2012 |

* cited by examiner

INTERVERTEBRAL CAGE APPARATUS AND SYSTEM AND METHODS OF USING THE SAME

RELATED APPLICATIONS

The present application is a divisional of U.S. patent application Ser. No. 14/422,750 filed Feb. 20, 2015, which is a national stage application under 35 U.S.C. § 371 of PCT Application No. PCT/US2013/056500, filed Aug. 23, 2013, which claims priority to U.S. Provisional Application No. 61/693,738 filed Aug. 27, 2012, entitled INTERVERTEBRAL CAGE APPARATUS AND SYSTEM AND METHODS OF USING THE SAME and U.S. Provisional Application No. 61/778,271 filed Mar. 12, 2013, entitled INTERVERTEBRAL CAGE APPARATUS AND SYSTEM AND METHODS OF USING THE SAME, the entire contents of each of which are hereby expressly incorporated by reference.

BACKGROUND OF THE INVENTION

Field of the Invention

This application relates to the field of intervertebral implants.

Description of the Related Art

Current intervertebral devices are designed using three major principles: the anatomical limitations of the surgical approach, optimization of bone graft volume to promote bone fusion, and optimization of the device contact with vertebral end plates to resist subsidence. Current devices are generally static in that they cannot change shape or volume. Thus, current devices are limited by anatomy and technique and consequently may not provide optimal bone graft volume or surface contact.

Other current intervertebral devices can change their shape and volume; however, these devices lack rigid components. As a result of this, while these devices are able to change their shape and/or volume, these devices do not provide for stable contact with vertebral end plates.

SUMMARY OF THE INVENTION

Certain embodiments of the present application relate to intervertebral implants and methods of using the same. For example, certain embodiments relate to an intervertebral cage, a deployment cable, a variable volume pouch, and/or an applicator device.

Some embodiments relate to an intervertebral cage that can be configured for positioning between two vertebrae and specifically between two vertebral end plates. In some embodiments, the intervertebral cage can be configured for expansion parallel to the vertebral end plates and/or for expansion perpendicular to the vertebral end plates. In some embodiments, the vertebral cage can be configured for use with a variable volume pouch and/or with a deployment cable. In some embodiments, for example, the variable volume pouch can be positioned within an internal volume of the intervertebral cage, and can be affixed to portions of the intervertebral cage. In some embodiments, for example, the expansion of the variable volume pouch can be facilitated by the deployment of the intervertebral cage, and in some embodiments, for example, the deployment of the intervertebral cage can be facilitated by the expansion of the variable volume pouch.

In some embodiments, the intervertebral cage can be deployed with a deployment cable. In some embodiments, the deployment cable can be configured to pass through all or portions of the intervertebral cage and to transmit force to the intervertebral cage to deploy the intervertebral cage. In some embodiments, the deployment cable can include an attachment feature configured to allow the deployment cable to be attached to the intervertebral cage, and in some embodiments, the deployment cable can include a locking feature configured to allow for locking the intervertebral cage into a deployed position with the deployment cable.

In some embodiments, for example, the intervertebral cage can be used with a variable volume pouch and with the deployment cable. In such embodiments, for example, the variable volume pouch can be positioned within a variable volume portion of the intervertebral cage and can be affixed to the intervertebral cage, at least in part, via the deployment cable. In one specific embodiment, the deployment cable can pass through a portion of the intervertebral cage and into and through a portion of the variable volume pouch, before passing again through a portion of the intervertebral cage. Advantageously, such use of the deployment cable and the variable volume pouch can simplify the affixation of the variable volume pouch to the intervertebral cage.

Some embodiments relate to methods of using a variable volume pouch in connection with an intervertebral cage to form an intervertebral cage apparatus. In some embodiments, such a method can include, for example, inserting a variable volume pouch into an intervertebral implant, affixing the variable volume pouch to all or portions of the intervertebral implant, and filling the variable volume pouch.

Some embodiments relate to methods of using the deployment cable in connection with the intervertebral cage. In some embodiments, for example, these methods can include inserting a deployment cable through all or portions of an intervertebral cage and applying a force to the intervertebral cage via the deployment cable.

Some embodiments relate to an intervertebral cage apparatus that can include, an intervertebral cage that can be moved from a first undeployed position to a second deployed position, and a deployment tool including a deployment cable having a first end and a second end, and a controller. In some embodiments, the first end of the deployment cable is connectable to a portion of the intervertebral cage and in some embodiments the second end of the deployment cable is connected to the controller. In some embodiments, the manipulation of the controller transmits force to the cable to move the intervertebral cage from the first position to the second position.

In some embodiments of the intervertebral cage apparatus, the intervertebral cage includes a body having a plurality of segments connected to each other by flexible connectors, and the movement of the cage from the first position to the second position decreases the distance between a proximal end and a distal end of the cage and increases a width of the body. In some embodiments of the intervertebral cage apparatus, the flexible connectors comprise living hinges. In some embodiments of the intervertebral cage apparatus, the intervertebral cage includes a lateral split. In some embodiments of the intervertebral cage apparatus, the intervertebral cage is configured to change its dimension along each of a longitudinal axis, a lateral axis, and a vertical axis when the intervertebral cage is moved from a first undeployed position to a second deployed position.

In some embodiments of the intervertebral cage apparatus, the intervertebral cage includes a first opening at a proximal end of the cage that can attach to the first end of the deployment cable, one or more openings at a distal end of the cage, and a second opening at a proximal end of the cage. In some embodiments, the cable can extend from the first opening to an opening at the distal end of the cage, and can extend from an opening at the distal end of the cage through the second opening and to the controller. In some embodiments of the intervertebral cage apparatus, the intervertebral cage includes a circuitous body partially defining an internal volume.

In some embodiments the intervertebral cage apparatus further includes a variable volume pouch having a first end with an opening and a sealed end located opposite the first end. In some embodiments, the variable volume pouch is positionable in an internal volume of the intervertebral cage such that the first end is proximate to a proximal aperture of the intervertebral cage. In some embodiments of the intervertebral cage apparatus, the variable volume pouch is affixed to the intervertebral cage, and in some embodiments, the variable volume pouch is affixed to the intervertebral cage using the deployment cable.

In some embodiments of the intervertebral cage apparatus, the intervertebral cage comprises a memory material, and in some embodiments, the memory material comprises a memory PEEK material.

Some embodiments relate to an intervertebral cage apparatus including an intervertebral cage comprising a memory material and that can move from a first undeployed position to a second deployed position, the intervertebral cage including a body having a plurality of segments connected to each other by flexible connectors. In some embodiments, the movement of the cage from the first position to the second position decreases the distance between a proximal end and a distal end of the cage and increases a width of the body.

In some embodiments of the intervertebral cage apparatus, the memory material comprises a memory PEEK material.

Some embodiments relate to a method of using an intervertebral cage apparatus. The method of using an intervertebral cage apparatus can include, for example, positioning an expandable intervertebral cage made of a memory material into an intervertebral disc space, the intervertebral cage including a circuitous body defining an internal volume and having a plurality of segments connected to each other by flexible connectors, and applying a trigger to the intervertebral cage. In some embodiments, the application of the trigger causes the memory material to transition shape via bending about the flexible connectors from an undeployed configuration to a deployed configuration.

Some embodiments relate to a method of using an intervertebral cage apparatus including positioning an expandable intervertebral cage into an intervertebral disc space, the intervertebral cage including a circuitous body defining an internal volume and having a plurality of segments connected to each other by flexible connectors, and applying a force to a deployment cable attached to the intervertebral cage. In some embodiments, the application of force causes bending about the flexible connectors to move the cage from an undeployed position to a deployed position.

In some embodiments, the method of using an intervertebral cage apparatus includes locking the position of the cage in the deployed position. In some embodiments, the method of using an intervertebral cage apparatus includes disengaging a portion of the deployment cable from the cage after the cage is in its deployed position. In some embodiments, the method of using an intervertebral cage apparatus includes delivering bone graft material through a proximal opening in the cage.

In some embodiments, the method of using an intervertebral cage apparatus includes positioning a variable volume pouch within the internal volume of the cage. In some embodiments of a method of using an intervertebral cage apparatus, the variable volume pouch is positioned within the internal volume of the cage prior to positioning the cage into the intervertebral disc space. In some embodiments of the method of using an intervertebral cage apparatus, the variable volume pouch is positioned within the internal volume of the cage after positioning the cage into the intervertebral disc space. In some embodiments of the method of using an intervertebral cage apparatus, the variable volume pouch is affixed to the cage. In some embodiments of the method of using an intervertebral cage apparatus, the variable volume pouch is affixed to the cage with the deployment cable, and the deployment cable passes through openings in the variable volume pouch. In some embodiments, the method of using an intervertebral cage apparatus includes filling the variable volume pouch through an opening in the variable volume pouch, said opening being located in a proximal aperture of the cage. In some embodiments, the method of using an intervertebral cage apparatus includes inserting a plug into the proximal aperture of the intervertebral cage.

Some embodiments relate to a system for deploying an intervertebral cage between two vertebrae which include an intervertebral cage apparatus configured to be moved from a first undeployed position to a second deployed position and an implantation tool with an outer cannula having a connector and a shaft having one or more pins. In some embodiments, a distal end of the intervertebral cage apparatus has a distal aperture. In some embodiments, the distal aperture additionally includes slots for the one or more pins. In some embodiments, the connector of the implantation tool has mating portions which may comprise teeth and a proximal portion of the intervertebral cage apparatus has cutouts configured to receive the mating portions.

In some embodiments, the method of using an intervertebral cage apparatus includes positioning an intervertebral cage apparatus into an intervertebral disc space, applying a relative force between a proximal end and a distal end of the intervertebral cage apparatus, and wherein an outer member of an implantation tool engages the proximal end and an inner member of the implantation tool engages the distal end. In some embodiments, applying the relative force is performed by applying a force in a distal direction to the proximal end while preventing translation of the distal end. In some embodiments, applying the relative force is performed by applying a force in a proximal direction to the distal end while preventing translation of the proximal end. In some embodiments, the distal end of the intervertebral cage apparatus includes slots and the method includes engaging pins to the distal end.

Some embodiments relate to a tool for implanting an intervertebral cage apparatus having a handle, a control member, an outer member attached to the handle, the outer member having a connector configured to engage a proximal end of an intervertebral cage apparatus, and an inner member attached to the control member, the inner member having pins configured to engage a distal end of the intervertebral cage apparatus. In some embodiments, the connector has a mating portion which protrudes distally from the connector and which is configured to engage a cutout on a proximal end of the intervertebral cage apparatus.

The foregoing is a summary and thus contains, by necessity, implications, generalizations, and omissions of detail; consequently, those skilled in the art will appreciate that the summary is illustrative only and is not intended to be in any way limiting. Other aspects, features, and advantages of the devices and/or processes and/or other subject matter described herein will become apparent in the teaching set forth herein. The summary is provided to introduce a selection of concepts in a simplified form that are further described below in the detailed description. This summary is not intended to identify key features or essential features of the claimed subject matter, nor is it intended to be used as an aide in determining the scope of the claimed subject matter.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through the use of the accompanying drawings.

DETAILED DESCRIPTION

The Intervertebral Cage

Figure 1A:
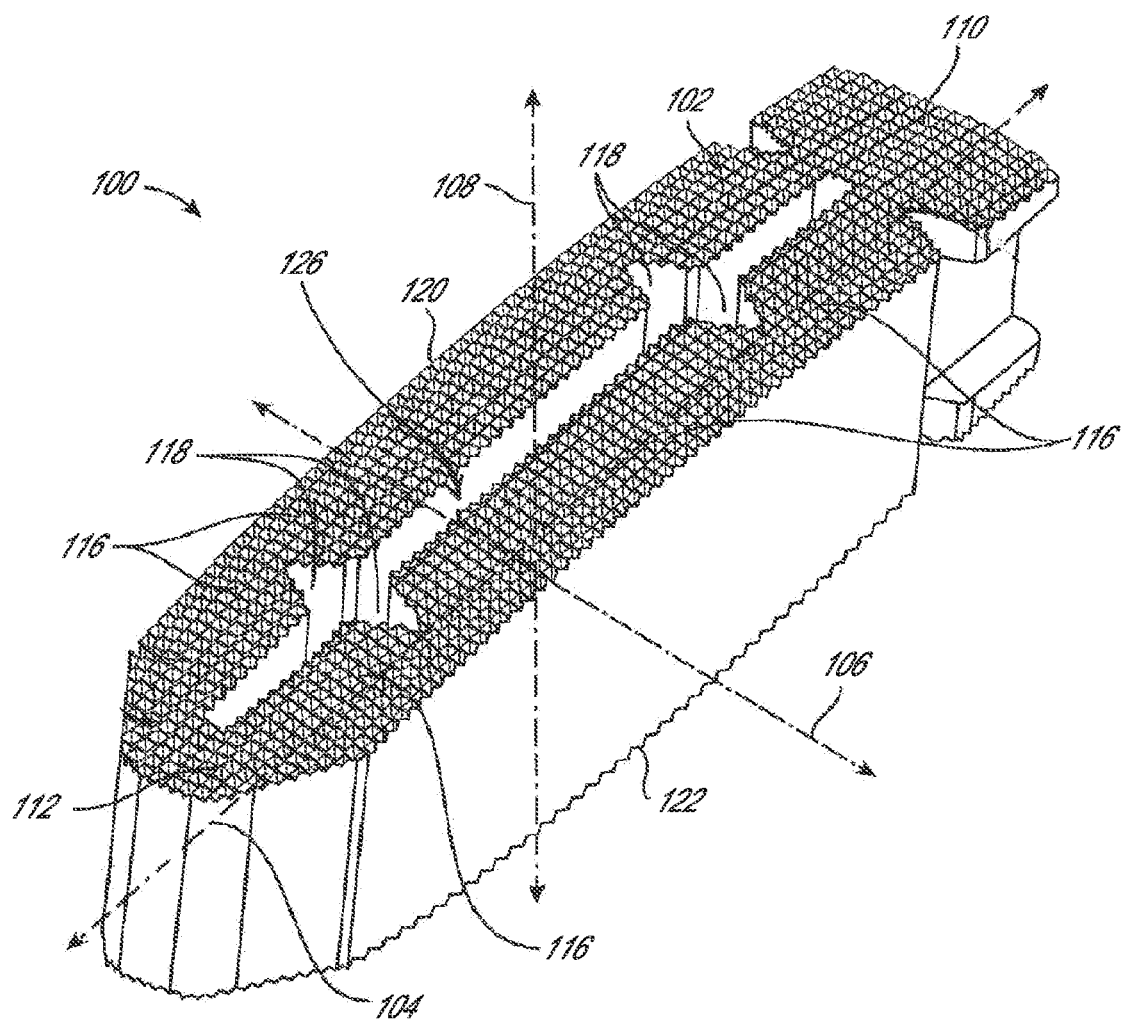
FIG. 1A is a perspective view of one embodiment of an intervertebral cage in an undeployed position.
Figure 1B:
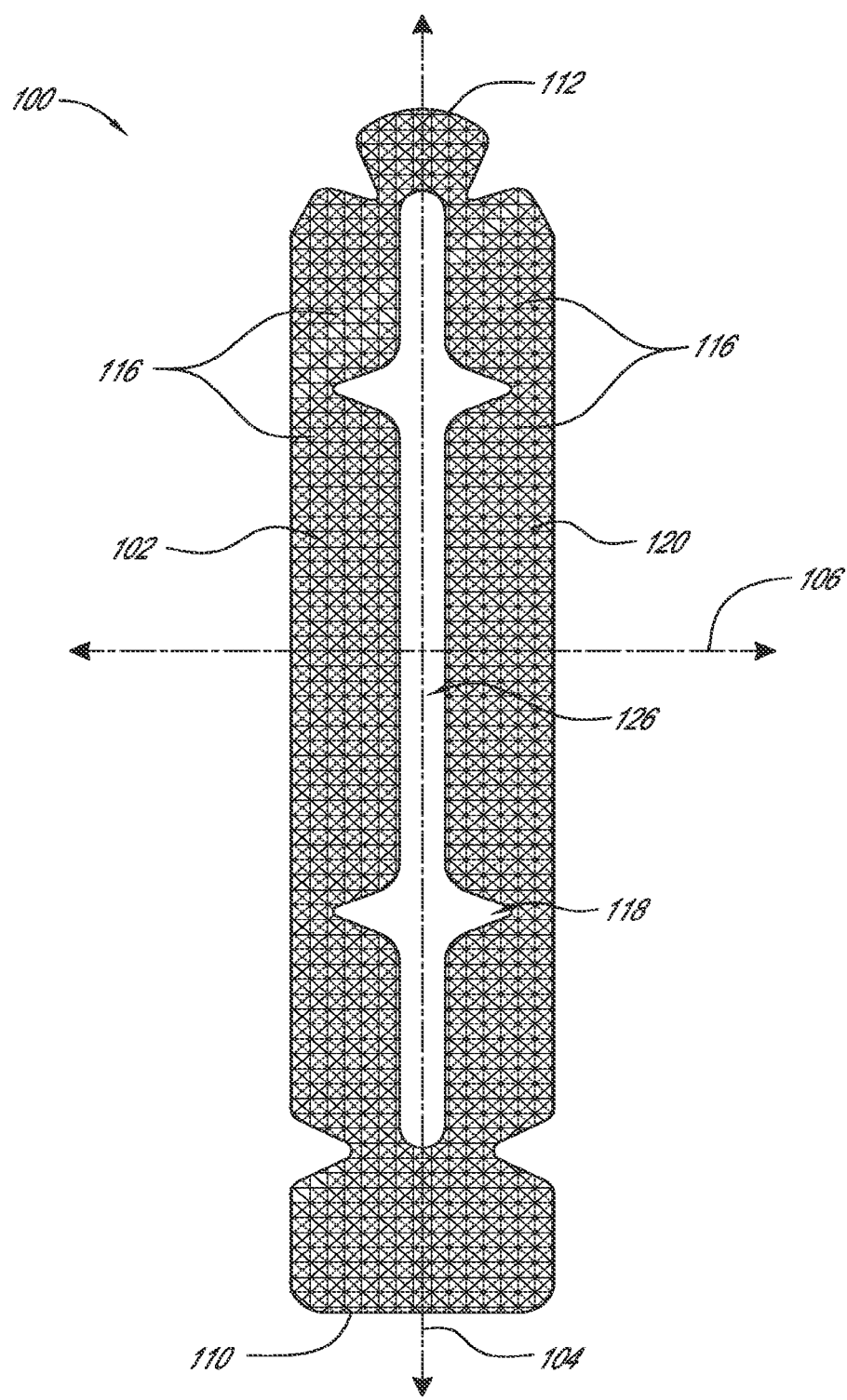
FIG. 1B is a top view of one embodiment of an intervertebral cage in an undeployed configuration.
Figure 2A:
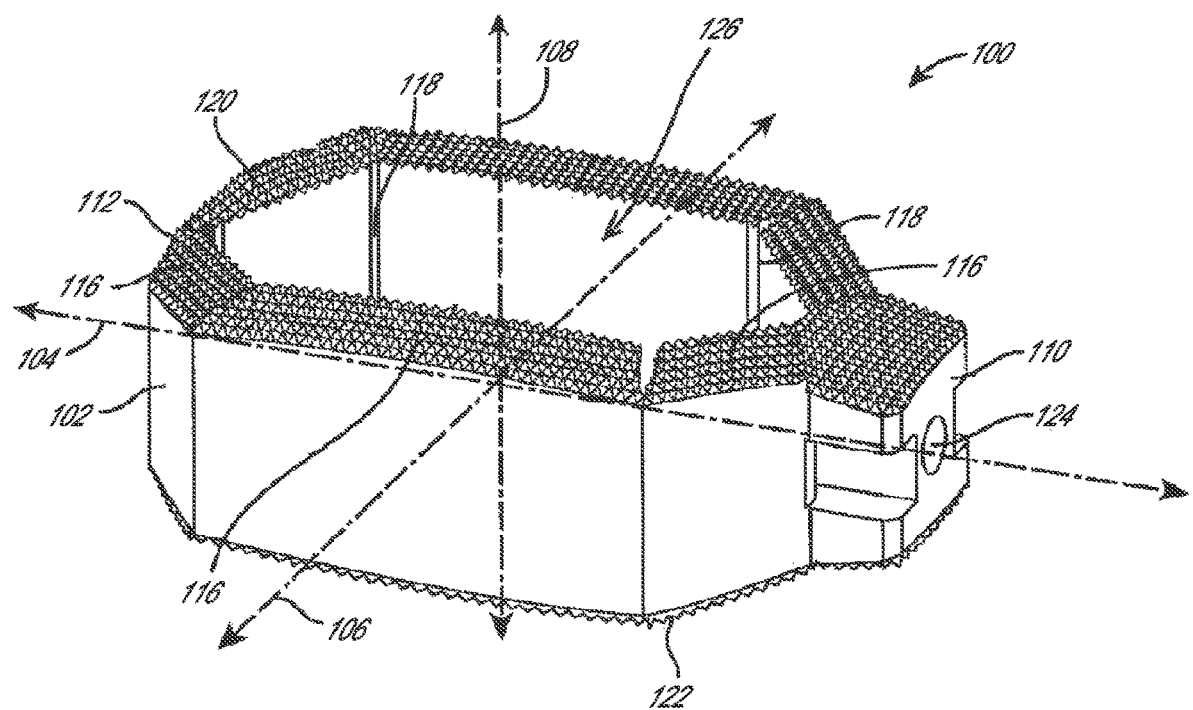
FIG. 2A is a perspective view of one embodiment of an intervertebral cage in a deployed configuration.
Figure 2B:
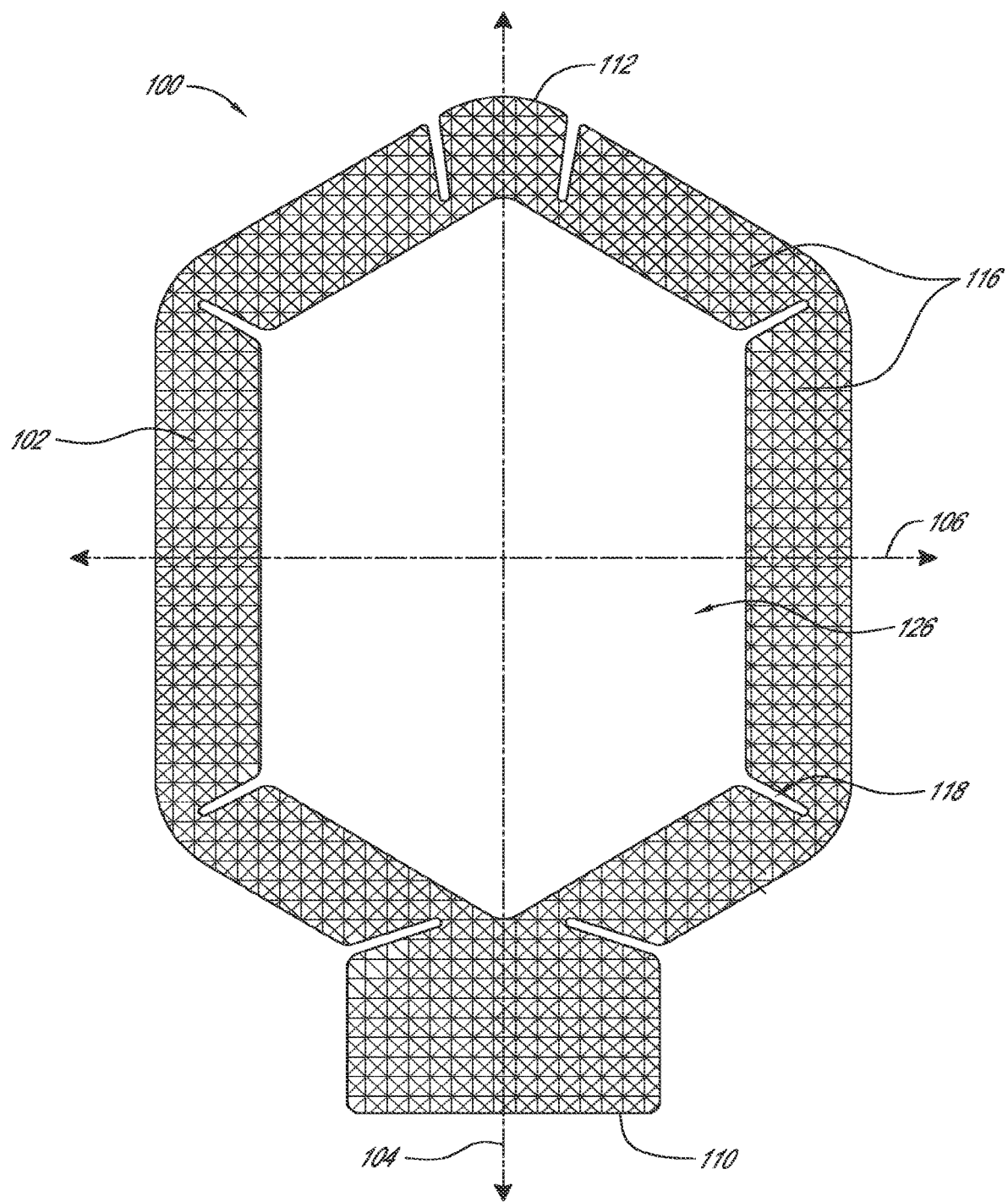
FIG. 2B is a top view of one embodiment of an intervertebral cage in a deployed configuration.

As shown in FIGS. 1A and 1B and in FIGS. 2A and 2B, an intervertebral implant, preferably an intervertebral cage 100 is provided. Although some details of the intervertebral cage 100 and methods of use are provided herein, further details can be found in U.S. Publication No. 2012/0083887 published on Apr. 5, 2012, entitled "Intervertebral Device and Methods of Use," and in U.S. Publication No. 2012/0083889 published on Apr. 5, 2012, entitled "Intervertebral Device and Methods of Use," both of which are incorporated herein in their entirety by reference. Both of these publications are further found attached in Appendix A, which material constitutes part of the present application.

The intervertebral cage 100 can be configured for positioning between two vertebrae and specifically for positioning between the end plates of two vertebrae. The intervertebral cage 100 can be positioned in an undeployed configuration as depicted in FIGS. 1A and 1B and can be positioned in a deployed configuration as depicted in FIGS. 2A and 2B. In some embodiments, and as depicted in FIGS. 1A-B and 2A-B, the change of the intervertebral cage 100 from an undeployed configuration to a deployed configuration can result in a change of the dimensions and shape of the intervertebral cage 100.

The intervertebral cage 100 can comprise a body 102. The body 102 can be configured to contact the two vertebrae between which the intervertebral cage 100 is positioned and/or to transfer force from one of the vertebrae between which the intervertebral cage 100 is positioned to the other of the vertebrae between which the intervertebral cage is positioned. The body 102 can comprise a variety of shapes and sizes and can be made from a variety of materials.

In some embodiments, for example, the body 102 can comprise a circuitous body defining a perimeter and an internal volume. In some embodiments, the body 102 can be sized and shaped for positioning between two vertebrae, and thus, can comprise dimensions and shapes that approximate the dimensions and shape of the space between the two vertebrae.

In some embodiments, the body 102 can comprise a biocompatible material including, for example, a natural biocompatible material, a synthetic biocompatible material, a metallic biocompatible material, and/or any other desired biocompatible material. In some specific embodiments, the body 102 can be made of polyetherketone (PEK), polyetherimide (PEI), such as Ultem, ultrahigh molecular weight polyethylene (UHMPE), polyphenylene, polyether-ether-ketone (PEEK), or any other desired biocompatible material. In some embodiments, the body 102 can comprise a memory material. In some specific embodiments, the body 102 can comprise a memory PEEK material such as, for example, PEEK Altera™. In one such embodiment in which a memory material is used for the body 102, the body 102 can be configured such that the deployed configuration is the first position to which the body 102 returns when the memory material is triggered and that the undeployed configuration is the second position. In such an embodiment, the body 102 of the intervertebral cage 100 can be positioned within an intervertebral space when the body 102 is in the undeployed, second position. After the body 102 has been properly positioned within the intervertebral space, the memory material can be triggered and the body can return to the deployed, first position.

The body 102 can have a proximal end 110 and a distal end 112. In some embodiments, the proximal end 110 and/or the distal end 112 can be an integral part of the body 102 and can partially define the internal volume of the body 102. In some embodiments, the proximal end 110 of the body 102 can be configured for interaction with an insertion tool to allow insertion of the intervertebral cage 100 and for the deployment of the intervertebral cage 100. In some embodiments, and as seen in FIG. 2A, the proximal end 110 of the body 102 can comprise a proximal aperture 124. In some embodiments, for example, the proximal aperture 124 can extend through the proximal end 110 of the body 102 and into the internal volume 126 of the body 102. Advantageously, in embodiments in which the proximal aperture 124 extends through the proximal end 110 of the body 102 and into the internal volume 126 of the body 102, the proximal aperture 124 can provide access to the internal volume 126 and/or components or features of an intervertebral cage apparatus located within the internal volume 126. The proximal end 110 can comprise a variety of shapes and sizes. Similarly, the proximal aperture 124 can comprise a variety of shapes and sizes.

The distal end 112 of the body 102 can be configured to facilitate insertion of the intervertebral cage 100 between the vertebrae. In some embodiments, for example, the distal end 112 of the body 102 can comprise a tapered and/or pointed shape to facilitate insertion of the body 102 into the space between the vertebrae. Advantageously, such a tapered and/or pointed shape to the distal end of the body 102 can facilitate in achieving adequate separation between the vertebrae and/or can minimize the insertion force required to insert the body 102 of the intervertebral cage 100 into the space between the vertebrae.

As seen in FIG. 1A, a longitudinal axis 104 of the body 102 can extend between the proximal end 110 and the distal end 112 of the body. As further seen in FIG. 1A, the body 102 can comprise a top 120 and a bottom 122. In some embodiments, the top 120 and the bottom 122 can each be configured for interaction with one of the vertebrae between which the intervertebral cage 100 is positioned, and specifically for interaction with one of the end plates of one of the vertebrae between which the intervertebral cage 100 is positioned. As also seen in FIG. 1A, the body 102 can define a vertical axis 108 extending perpendicular to the longitudinal axis 104 and between the top 120 and the bottom 122 of the body 102. As further seen in FIG. 1A, the body 102 can define a lateral axis 106 extending perpendicular to both the longitudinal axis 104 and the vertical axis 108.

As seen in FIGS. 1A-B and in FIGS. 2A-B, some embodiments of the body 102 can comprise segments 116 connected to each other by flexible connectors 118, which can comprise any bendable connector, including, for example, one or several living hinges. In some embodiments, for example, the segments 116 can comprise elongate members which are bounded by the flexible connectors 118. The flexible connectors 118 can, in some embodiments, be located on an interior surface of the body 102 proximate to the internal volume 126, and in some embodiments, the flexible connectors 118 can be located on an exterior surface of the body 102. In some embodiments, the flexible connectors 118 can comprise portions of the body 102 that are configured to bend. In some embodiments, the flexible connectors 102 can be discrete elements in that the bending may be localized in one or several positions on the body 102, and in some embodiments, the flexible connectors 102 may be non-discrete elements in that the bending may not be localized, but rather occur over all or large portions of the body 102. In some embodiments in which the flexible connectors 118 comprise discrete elements, the flexible connector can comprise a shape, a feature, a material characteristic, or any other aspect that concentrates stresses and/or deformation. As specifically depicted in FIGS. 1A-B and 2A-B, in some embodiments, the flexible connectors 118 can comprise narrowed portions of the body 102 and/or cutouts into the body 102 to allow localized deformations of the body 102 when the body 102 is moved from an undeployed configuration to a deployed configuration.

The segments 116 and the flexible connectors 118 can comprise a variety of shapes and sizes. In some embodiments, for example, the shapes and sizes of the segments 116 and/or the flexible connectors 118 can be determined by the desired size of the intervertebral cage 100, the desired deployment force, the desired deployed resulting shape, the desired undeployed shape, and/or a number of other considerations.

As seen in FIGS. 1A-B and 2A-B, the combination of the segments 116 and the flexible connectors 118 allow deployment of the body 102 of the intervertebral cage 100, which deployment decreases the distance between the proximal end 110 and the distal end 112 and increases the width of the body 102 as measured along the lateral axis 106.

Figure 3:
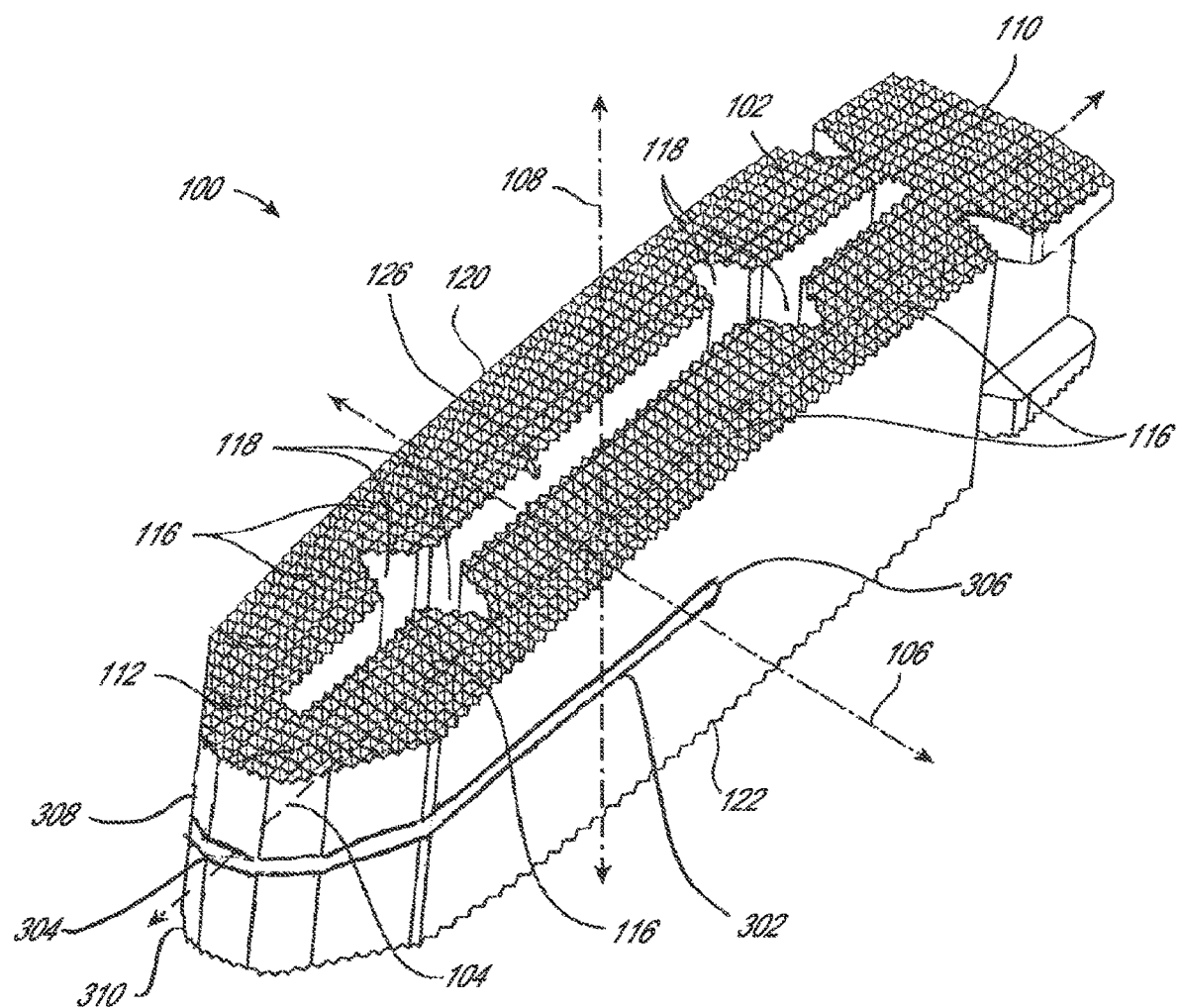
FIG. 3 is a perspective view of one embodiment of an intervertebral cage including a lateral split in an undeployed position.

In some embodiments, an intervertebral cage 100 can be configured such that dimensions of the intervertebral cage 100 vary along one, two, or three of the above discussed axes 104, 106, 108 when the intervertebral cage 100 is moved from an undeployed configuration to a deployed configuration. FIG. 3 depicts such an embodiment of an intervertebral cage 300 configured for dimensional change along three of its axes 104, 106, 108. The intervertebral cage 300 depicted in FIG. 3 comprises a body 102 having a proximal end 110 and a distal end 112. The body 102 defines a longitudinal axis 104 extending down the center of the body 102 and between the proximal end 110 and the distal end 112. The body 102 of the intervertebral cage 300 depicted in FIG. 3 further comprises a top 120 and a bottom 122 and defines a vertical axis 108 extending between the top 120 and the bottom 122 and perpendicular to the longitudinal axis 104. The body 102 of the intervertebral cage 300 further defines a lateral axis 106 which extends perpendicular to both the longitudinal axis 104 and the vertical axis 108.

The body 102 of the intervertebral cage 300 depicted in FIG. 3 further comprises a plurality of segments 116 joined by flexible connectors 118. The segments 116 and flexible connectors 118 of the body 102 define an internal volume 126 of the body 102.

As also seen in FIG. 3, the body 102 of the intervertebral cage 300 comprises a lateral split 302. The lateral split 302 can be configured to allow the expansion of the body 102 of the intervertebral cage 300. In some embodiments, for example, the lateral split 302 can be configured to allow the expansion of all or a portion of the body 102 of the intervertebral cage 300 in a direction perpendicular to the lateral split 302.

The lateral split 302 can comprise a variety of sizes and shapes. In some embodiments, for example, the lateral split 302 can extend from one end of the body 102 towards another end of the body 102. As specifically depicted in FIG. 3, the lateral split 302 extends from the distal end 112 of the body 102 towards the proximal end 110 of the body 102. The length of the lateral split 302 can vary based on the desired amount of expansion allowed by the lateral split 302. In some embodiments, for example, the lateral split 302 can extend for 5% of the length of the body, 10% of the length of the body, 25% of the length of the body, 50% of the length of the body, 75% of the length of the body, 90% of the length of the body, or any other intermediate or other desired percent of the length of the body as measured along one of the axes 104, 106, 108 of the body 102.

As further seen in FIG. 3, the lateral split 302 comprises a first end 304 and a second end 306. As specifically depicted in FIG. 3, the first end 304 of the lateral split 302 is located proximate to the distal end 112 of the body 102 and the second end 306 of the lateral split 302 is located approximately in the middle of the body 102. As also seen in FIG. 3, the lateral split 302 divides the body 102 at least partially into a top portion 308 and a bottom portion 310. As seen in FIG. 3, the top portion 308 is located between the top 120 of the body 102 of the intervertebral cage 300 and the lateral split 302 and the bottom portion 310 is located between the bottom 122 of the body 102 of the intervertebral cage 300 and the lateral split 302. Advantageously, the division of the body 102 into a top portion 308 and into a bottom portion 310 by a lateral split 302 allows the expansion of the body 102 of the intervertebral cage 300. In some embodiments, for example, this expansion of the body 102 of the intervertebral cage 300 can be perpendicular to the lateral split 302, and in some embodiments, this expansion of the body 102 can be nonperpendicular to the lateral split 302. As specifically depicted in FIG. 3, the top portion 308 and the bottom portion 310 of the body 102 allow the expansion of the body 102 in a direction parallel to the lateral axis 106 by the expansion of the lateral split 302.

The Variable Volume Pouch

Figure 4A:
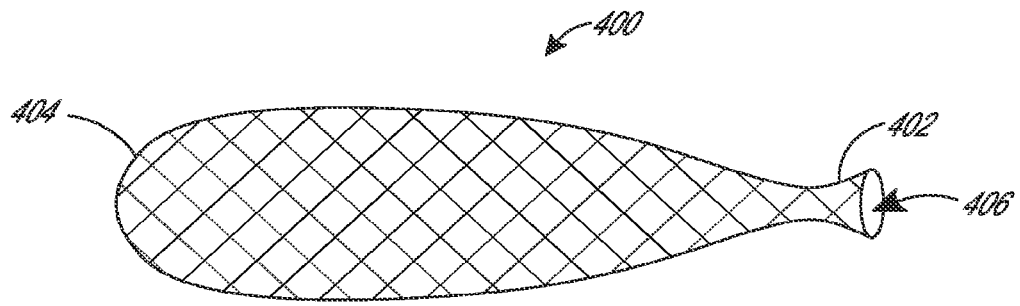
FIG. 4A is a perspective view of one embodiment of a variable volume pouch in an unexpanded configuration.
Figure 4B:
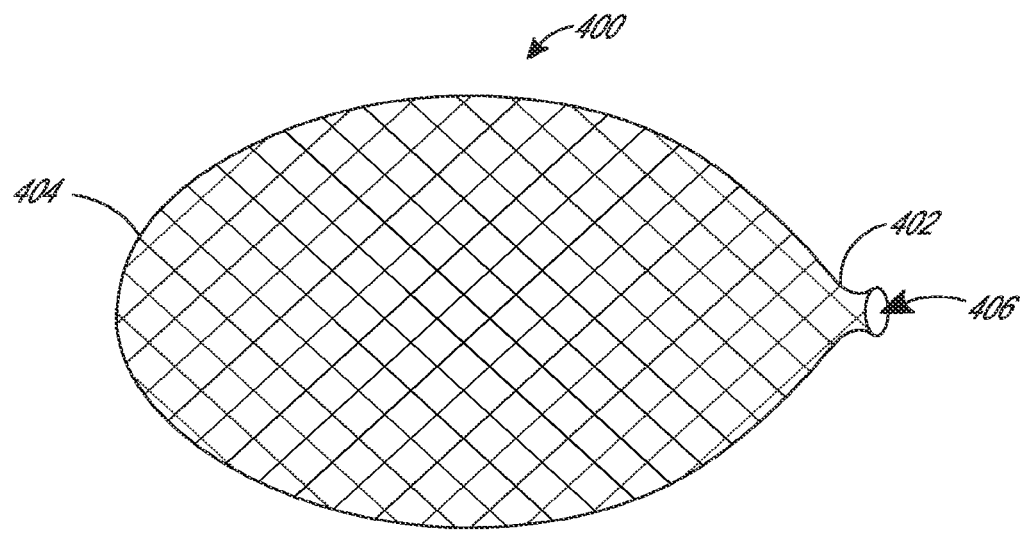
FIG. 4B is a perspective view of one embodiment of a variable volume pouch in an expanded configuration.

Some embodiments of an intervertebral cage apparatus can include a variable volume pouch. FIG. 4A depicts a perspective view of one embodiment of a variable volume pouch 400 in an unexpanded state and FIG. 4B depicts one embodiment of a variable volume pouch 400 in an expanded state. The variable volume pouch 400 can be configured for expansion in response to receiving material in an internal portion of the variable volume pouch 400. In some embodiments, the variable volume pouch 400 can be configured to resist compressive forces when the variable volume pouch 400 is filled with material. One example of a variable volume pouch is the OptiMesh® Deployable Grafting System available from Spineology, Inc. Although some details of the variable volume pouch 400 and methods of use are provided herein, further details can be found in U.S. Pat. No. 5,549,679 published on Mar. 1, 1995, entitled "Expandable Fabric Implant For Stabilizing the Spinal Motion Segment," and in U.S. Pat. No. 5,571,189 published on Nov. 5, 1996, entitled "Expandable Fabric Implant For Stabilizing the Spinal Motion Segment," both of which are incorporated herein in their entirety by reference. Both of these patents are further found attached in Appendix A, which material constitutes part of the present application.

The variable volume pouch can comprise a variety of shapes and sizes. In some embodiments, for example, the variable volume pouch 400 can be shaped to allow uniform expansion of the variable volume pouch 400 when material is added into the internal portion of the variable volume pouch 400. In some embodiments, for example, the variable volume pouch can be approximately spherical, ovular, elongate, cylindrical, rectangular, or have any other desired shape. In the embodiment depicted in FIGS. 4A and 4B, the variable volume pouch 400 is approximately balloon shaped. As also seen in FIGS. 4A and 4B, the variable volume pouch 400 comprises a first end 402 and a second end 404 positioned opposite the first end 402. As seen in FIGS. 4A and 4B, the variable volume pouch 400 further comprises a single opening 406 located at the first end 402.

In some embodiments, the variable volume pouch 400 can include features configured to allow the selectable sealing and/or closing of the opening 406. These features can include, for example, one or several tics, one or several drawstrings, one or several plugs, or any other mechanical or other feature configured to allow the sealing and/or closing of the opening 406.

The variable volume pouch 400 can comprise a variety of materials. In some embodiments, the variable volume pouch can comprise a natural material, a synthetic material, a man-made material, a polymer, composite material, an elastic material, an inelastic material and/or any other desired material. In some embodiments, and as depicted in FIGS. 4A and 4B, the variable volume pouch 400 can comprise a woven material. Advantageously, a woven material can allow expansion of the variable volume pouch 400 to a desired maximum size.

The variable volume pouch 400 can comprise a variety of sizes. In some embodiments, the variable volume pouch 400 can be sized to allow placement between two vertebrae. Specifically, in some embodiments, the variable volume pouch 400 can be sized to fit between two vertebrae and specifically between the end plates of two vertebrae.

The Intervertebral Cage Apparatus

Figure 5A:
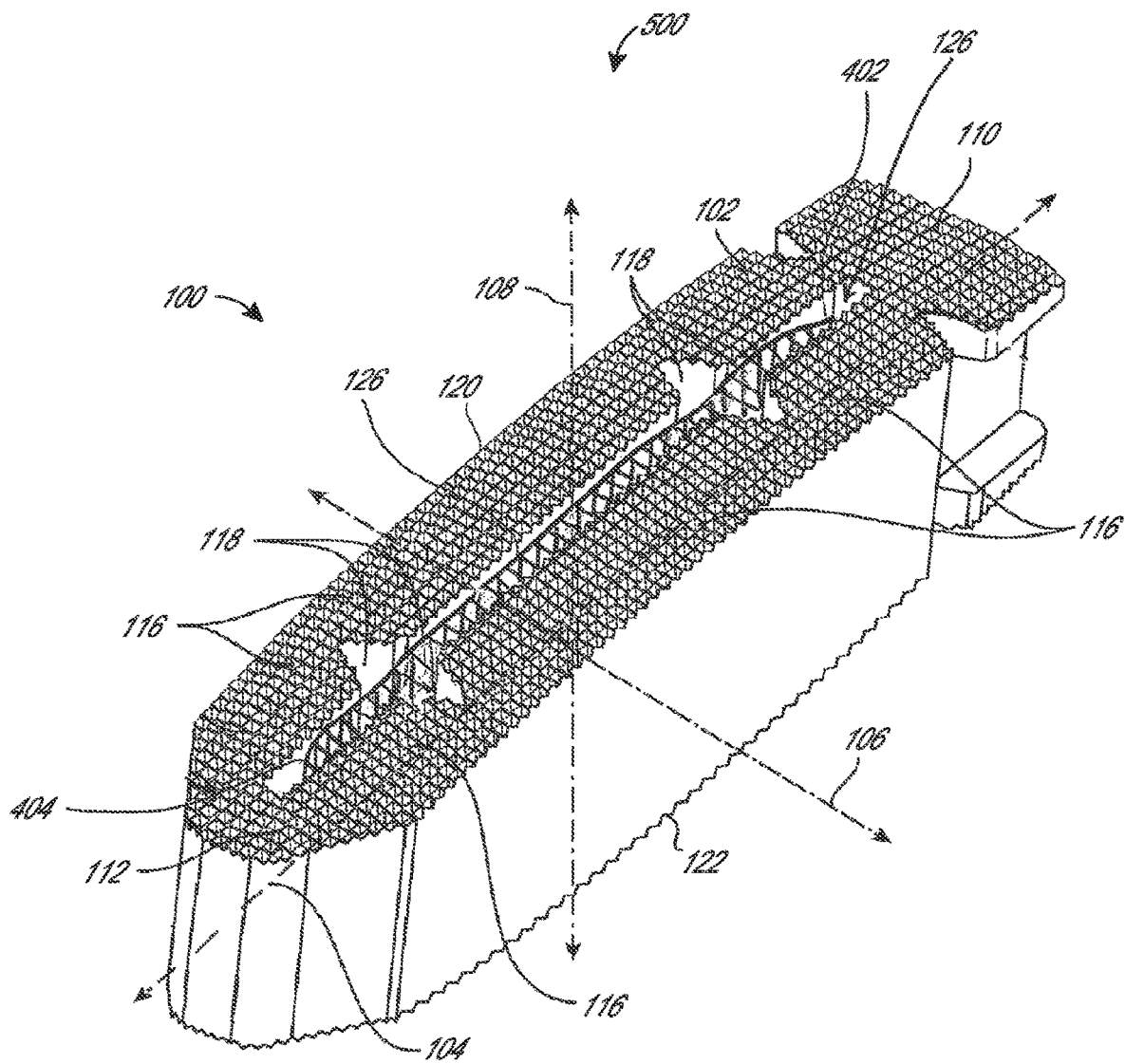
FIG. 5A is a perspective view of one embodiment of an intervertebral cage apparatus including an intervertebral cage and a variable volume pouch in an undeployed configuration.
Figure 5B:
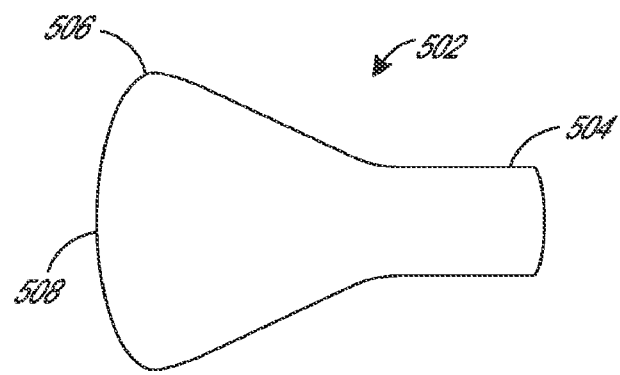
FIG. 5B is a side view of one embodiment of a plug.

Some embodiments relate to an intervertebral cage apparatus. FIG. 5A depicts a perspective view of one embodiment of the intervertebral cage apparatus 500. The intervertebral cage apparatus 500 comprises the intervertebral cage 100. The intervertebral cage 100 depicted in FIG. 5A comprises the features of the intervertebral cage 100 depicted in FIG. 1A, including a body 102 having a proximal end 110 and a distal end 112. The body 102 defines a longitudinal axis 104 extending down the center of the body 102 and between the proximal end 110 and the distal end 112. The body 102 of the intervertebral cage 100 depicted in FIG. 5A further comprises a top 120 and a bottom 122 and defines a vertical axis 108 extending between the top 120 and the bottom 122 and perpendicular to the longitudinal axis 104. The body 102 of the intervertebral cage 300 further defines a lateral axis 106 which extends perpendicular to both the longitudinal axis 104 and the vertical axis 108.

The body 102 of the intervertebral cage 100 depicted in FIG. 5A further comprises a plurality of segments 116 joined by flexible connectors 118. The segments 116 and flexible connectors 118 of the body 102 define an internal volume 126 of the body 102.

As seen in FIG. 5A, the intervertebral cage apparatus 500 further includes the variable volume pouch 400 located within the internal volume 126 of the intervertebral cage 100. In some embodiments, the variable volume pouch 400 can be affixed to all or portions of the intervertebral cage 100. In some embodiments, for example, the variable volume pouch 400 can be inserted into the internal volume 126 of the intervertebral cage 100 such that the second end 404 of the variable volume pouch 400 is proximate to the distal end 112 of the intervertebral cage 100 and the first end 402 is proximate to the proximal end 110 of the intervertebral cage 100. In some advantageous embodiments, in which the first end 402 is proximate to the proximal end 110 of the intervertebral cage 100, the opening 406 of the variable volume pouch 400 is located proximate to the proximate aperture 124 of the body 102 of the intervertebral cage 100. Thus, in some embodiments, the variable volume pouch 400 can be inserted into the internal volume 126 of the body 102 of the intervertebral cage 100 through the proximal aperture 124. In such an embodiment, after the variable volume pouch 400 is inserted into the internal volume 126 of the body 102 via the proximal aperture 124, the variable volume pouch 400 can be partially or completely affixed to the body 102 of the intervertebral cage 100. In some embodiments, the variable volume pouch 400 can be affixed to the body 102 of the intervertebral cage 100 such that the expansion of the variable volume pouch 400 can result in the deployment of the body 102 of the intervertebral cage 100 and in some embodiments, the affixation of the variable volume pouch 400 to the body 102 of the intervertebral cage 100 can result in the expansion of the variable volume pouch 400 when the body 102 of the intervertebral cage 100 is deployed.

In some embodiments, the intervertebral cage apparatus 500 can further comprise a plug 502. The plug 502 can be configured to sealingly fit within the proximal aperture 124 to seal the proximal aperture, to secure the first end 402 of the variable volume pouch 400 to the proximal end 110 of the intervertebral cage 100, and to seal the opening 406 of the variable volume pouch. In some embodiments, the plug 502 can be further configured to facilitate in the deployment of the intervertebral cage 100. The plug 502 can comprise a variety of shapes and sizes, and can be made from a variety of materials, including, for example, all of the materials from which the intervertebral cage 100 can be made.

In some embodiments, the plug 502 can comprise a proximal shaft 504 and a distal head 506. The proximal shaft 504 can comprise a variety of shapes and sizes. In some embodiments, the proximal shaft 504 can be sized and shaped to seal the proximal aperture 124, and specifically can be sized and shaped with larger dimensions than the proximal aperture 124. In some embodiments, the configuration of the proximal shaft 504 with dimensions larger than the dimensions of the proximal aperture 124 can facilitate the retention of the plug 502 in the proximal aperture 124.

In some embodiments, the distal head 506 can comprise a variety of shapes and sizes. In some embodiments, the distal head 506 can be conical shaped, having a distal base 508, and extending towards the apex in the direction of the proximal shaft 504. The distal head 506 can be shaped, in some embodiments, to facilitate in deploying the intervertebral cage 100.

Figure 6A:
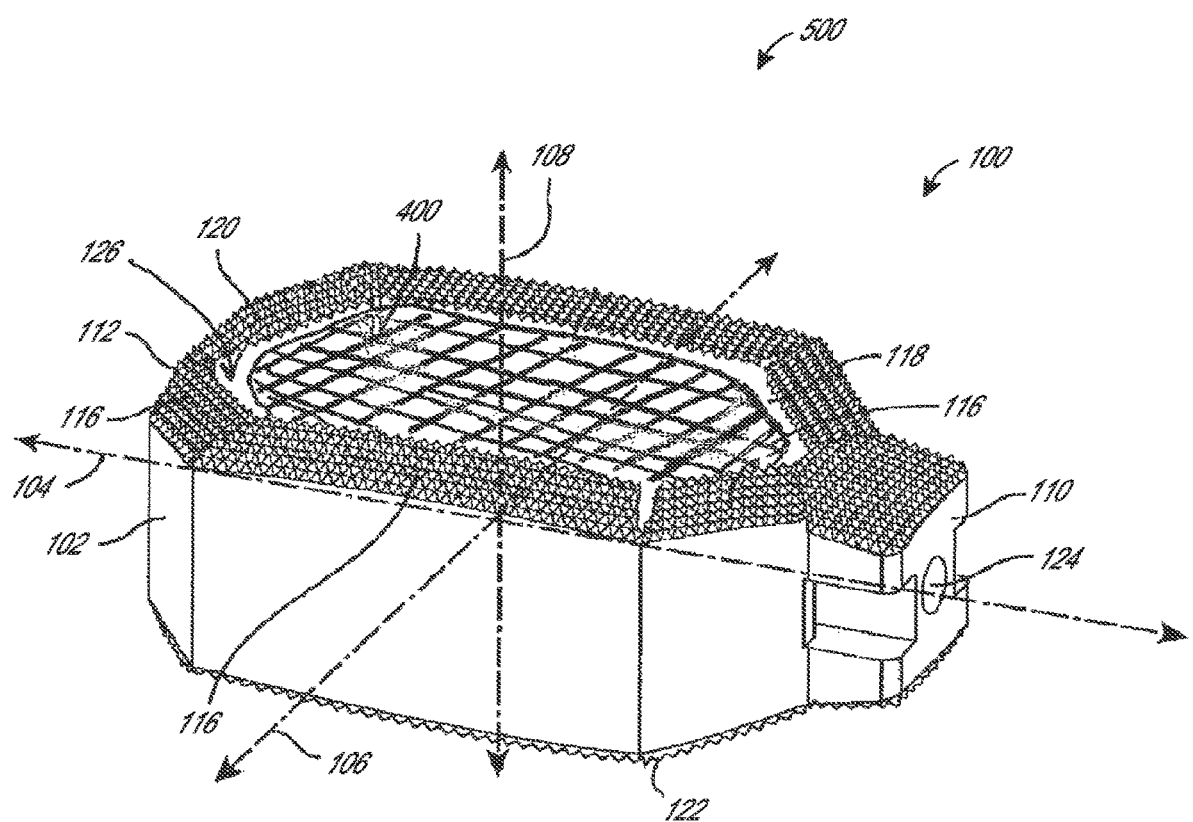
FIG. 6A is a perspective view of one embodiment of an intervertebral cage apparatus including an intervertebral cage and a variable volume pouch in a deployed configuration.

FIG. 6A depicts one embodiment of the intervertebral cage apparatus 500 in a deployed configuration in which the body 102 of the intervertebral cage 100 is deployed and in which the variable volume pouch 400 is in its expanded configuration. As seen in FIG. 6A, the variable volume pouch 400 in its expanded configuration fills and/or substantially fills the internal volume 126 of the intervertebral cage 100.

Figure 6B:
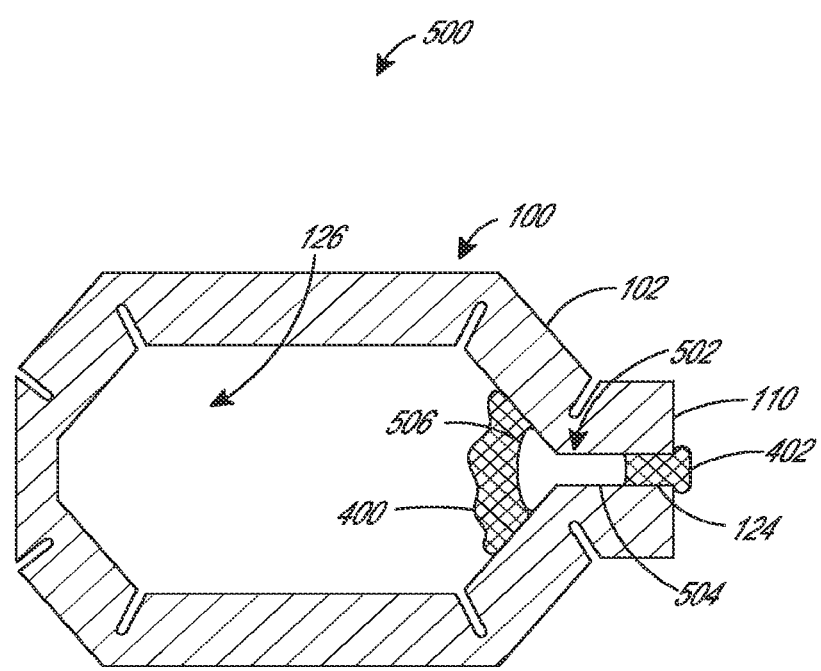
FIG. 6B is a top cutaway view of one embodiment of an intervertebral cage apparatus in a deployed configuration.

FIG. 6B is a cutaway top-view of the intervertebral cage apparatus 500 in a deployed configuration. As seen in FIG. 6B, the proximal shaft 504 of the plug 502 is located in the proximal aperture 124 of the body 102 of the intervertebral cage 100. As also seen in FIG. 6B, the proximal shaft 504 of the plug has expanded the diameter of the proximal aperture 124, and is thereby secured within the proximal aperture 124. As also seen in FIG. 6B, the plug 502 is positioned within the proximal aperture 124 such that a portion of the first end 402 of the variable volume pouch 400 is between the proximal shaft 504 and the wall of the proximal aperture, thereby securing the variable volume pouch 400.

FIG. 6B further depicts the distal head 506 of the plug 502 extending into the internal volume 126 of the intervertebral cage 100. As seen in FIG. 6B, the distal head 506 is engaging portion of the body 102, to thereby bias the body 102 of the intervertebral cage 100 towards a deployed configuration.

In some embodiments, in which the plug 502 is used in connection with the intervertebral cage apparatus 500, the variable volume pouch 400 can be inserted into the intervertebral cage 100 through the proximal aperture 124 and positioned such that the first end 402 of the variable volume pouch 400 and the opening 406 are proximate to the proximal aperture 124. In some embodiments, the variable volume pouch 400 can be at least partially affixed to the intervertebral cage 100. After the variable volume pouch 400 is inserted into the intervertebral cage 100, positioned, and if desired, at least partially affixed to the intervertebral cage 100, the variable volume pouch can be filled and/or the intervertebral cage 100 can be deployed.

In some embodiments, the plug 502 can be inserted into the intervertebral cage 100, and partially into the internal volume 126 of the intervertebral cage, by inserting the plug 502 into and through the proximal aperture 124 from the proximal end 110 of the intervertebral cage 100 towards the distal end 112 of the intervertebral cage 100. Advantageously, the insertion of the plug 502 can affix the variable volume pouch 400 to the proximal end 110 of the intervertebral cage, can seal the opening 406 of the variable volume pouch 400, and can assist in the deployment of the intervertebral cage 100.

In some embodiments, in which the plug 502, and specifically in which the distal head 506 and the proximal shaft 504 have a larger diameter than the proximal aperture 124, the insertion of the plug into and through the proximal aperture 124 from the proximal end 110 of the intervertebral cage 100 towards the distal end 112 of the intervertebral cage 100 can result in the deformation of the proximal aperture 124. In some embodiments, all or portions of the proximal aperture 124 may partially or completely elastically rebound after the insertion of the plug 502, and in some embodiments, all or portions of the proximal aperture 124 may not elastically rebound after the insertion of the plug 502.

Figure 7:
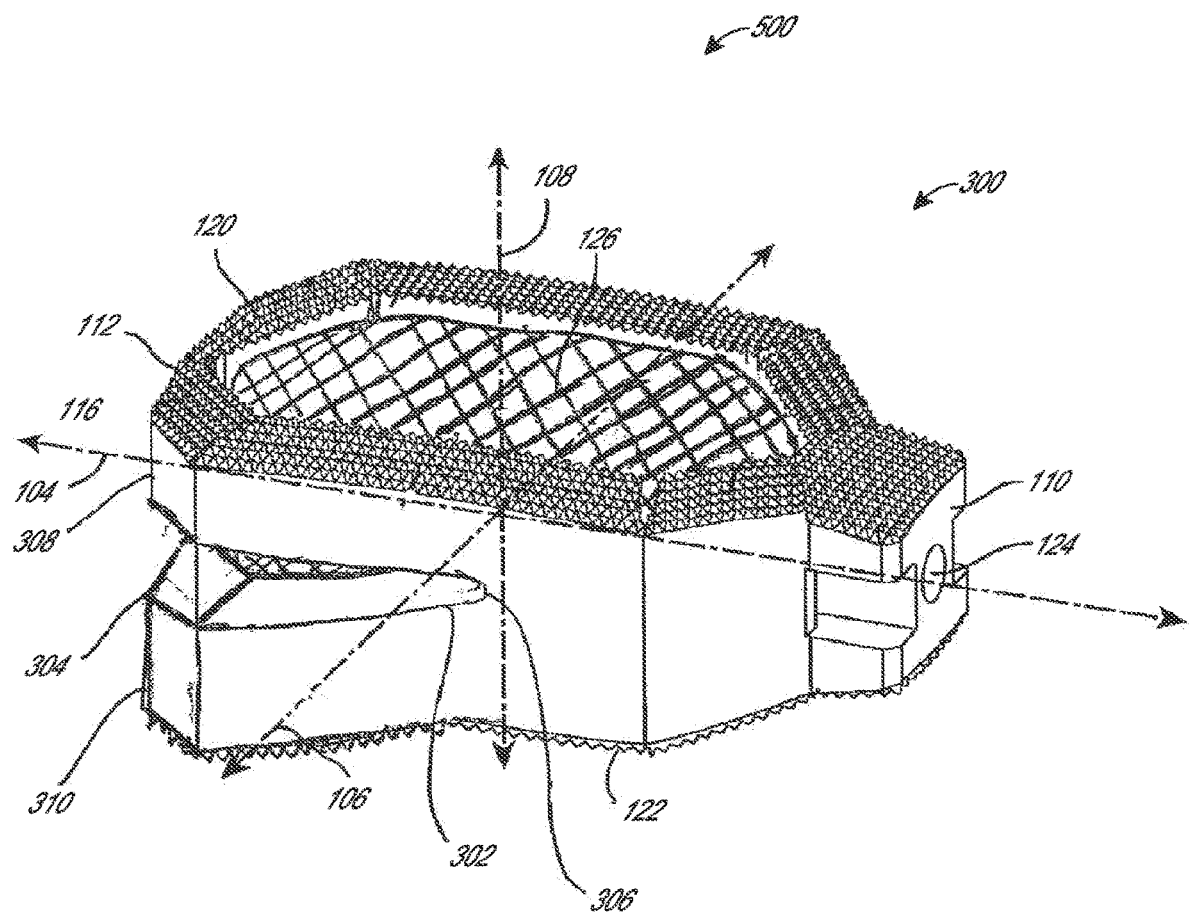
FIG. 7 is a perspective view of one embodiment of an intervertebral cage apparatus including a variable volume pouch and an intervertebral cage having a lateral split in a deployed configuration.

FIG. 7 depicts an alternative embodiment of the intervertebral cage apparatus 500. Specifically, FIG. 7 depicts an embodiment of the intervertebral cage apparatus 500 comprising a variable volume pouch 400 shown in this figure in its expanded state, and the intervertebral cage 300 comprising a lateral split 302 shown in its fully deployed configuration. As seen in FIG. 7, the intervertebral cage 300 is deployed in both the lateral direction 106 as measured along the lateral axis 106 and deployed in the vertical direction as measured along the vertical axis 108. As seen in FIG. 7, the variable volume pouch 400 substantially fills and/or fills the internal volume 126 of the intervertebral cage 300.

The Deployment System

Figure 8:
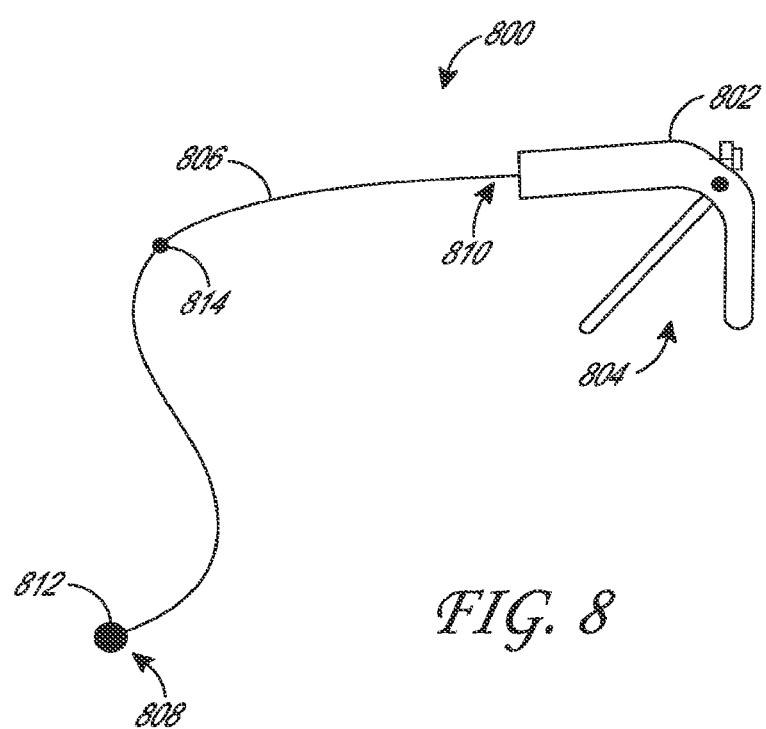
FIG. 8 is a schematic illustration of one embodiment of a deployment system.

Some embodiments relate to systems and devices for the insertion and deployment of an intervertebral cage apparatus 500 and/or of the intervertebral cage 100, 300. FIG. 8 depicts one embodiment of insertion deployment system 800. As seen in FIG. 8, the deployment system 800 can include a deployment tool 802. The deployment tool 802 can be configured to facilitate in the insertion of the intervertebral cage apparatus 500 and/or the intervertebral cage 100, 300 and to control the deployment of the intervertebral cage apparatus 500 and/or the intervertebral cage 100, 300.

The deployment tool 802 can comprise a variety of shapes and sizes and can comprise a variety of features. In some embodiments, for example, the deployment tool 802 can be a mechanical device, an electromechanical device and/or an electrical device. In some embodiments, for example, the deployment tool 802 can be manually operated, can be electrically controlled, and/or can be controlled using any other desired control technique. As depicted in FIG. 8, the deployment tool 802 comprises a control interface 804. The control interface 804 can be configured to allow a user to control the deployment tool 802 and the insertion and/or deployment of the intervertebral cage apparatus 500 and/or the intervertebral cage 100, 300. In some embodiments, for example, the control interface can comprise any feature, system, and/or module configured to receive user input and use that input to effect the deployment of the intervertebral cage apparatus 500 and/or the intervertebral cage 100, 300. As depicted in FIG. 8, the control interface 804 can comprise a simple manual control configured to apply a force to one end of a deployment cable 806.

In some embodiments in which the deployment tool 802 can be used in connection with other features to insert the intervertebral cage 100, 300. In such embodiments, the deployment tool 802 can be used with a rigid shaft. In one embodiment, the rigid shaft can comprise a proximal end that is affixed to the deployment tool 802 and a distal end configured to engage with the intervertebral cage 100, 300. In some embodiments, these features configured to engage with the intervertebral cage 100, 300 and located at the distal end of the rigid shaft can comprise one or several prongs (not shown) configured to engage portions of the intervertebral cage 100, 300. In some embodiments, the features configured to selectively affix the intervertebral cage 100, 300 to the deployment tool 802, can allow the manipulation and movement of the intervertebral cage 100, 300 along and/or about any of the axes 104, 106, 108 of the intervertebral cage 100, 300.

In some embodiments, the rigid shaft can be configured to allow the passage of the deployment cable 806 from the deployment tool 802 to the intervertebral cage 100, 300. In some embodiments, the deployment cable 806 can pass along the rigid shaft and/or through the rigid shaft from the deployment tool 802 to the intervertebral cage 100, 300. The passing of the deployment cable 806 from the deployment tool 802 to the intervertebral cage 100, 300 can be facilitated by one or several channels located within the rigid shaft. In some embodiments, these rigid channels can be located on an exterior surface of the rigid shaft, and or located within the rigid shaft. In some embodiments, the channels can extend the entire length of the rigid shaft, and/or along portions of the rigid shaft.

In some embodiments in which the deployment tool 802 is only used for deployment of the intervertebral cage 100, 300 a separate insertion tool and/or tools can be used in the insertion of the intervertebral cage 100, 300. Some embodiments of such an insertion tool and/or implantation tool can be found in U.S. Publication No. 2012/0083887 published on Apr. 5, 2012 which is incorporated herein in its entirety by reference. This publication is attached in Appendix A, and constitutes part of the present application.

The deployment cable 806 can be configured to transfer a force from the deployment tool 802 to the intervertebral cage apparatus 500 and/or the intervertebral cage 100, 300. In some embodiments, the deployment cable 806 can be configured to facilitate the deployment of the intervertebral cage apparatus 500 and/or the intervertebral cage 100, 300 and/or to facilitate in maintaining the intervertebral cage apparatus 500 and/or the intervertebral cage 100, 300 in a deployed configuration. In some embodiments, the deployment cable 806 can be configured for use as a marker, and specifically, can be used as a marker to indicate the position of the intervertebral cage 100, 300 and/or to determine whether and to what extent the intervertebral cage 100, 300 has been deployed. In some embodiments, for example, the deployment cable 806 can include regularly spaced features that can allow determination of whether and/or to what extent the intervertebral cage 100, 300 is deployed by allowing the determination of the length of the deployment cable 806 within the intervertebral cage 100, 300 As the deployment of the intervertebral cage 100, 300 may, in some embodiments, change a dimension of the intervertebral cage 100, 300 the determination of the length of the portion of the deployment cable 806 located within the intervertebral cage can facilitate in determining whether and/or to what extent the intervertebral cage 100, 300 is deployed.

The deployment cable 806 can comprise a variety of shapes and sizes and can be made from a variety of materials. In some embodiments, the deployment cable 806 can comprise any shape and size and can be made from any material capable of applying and withstanding the forces necessary to deploy the intervertebral cage apparatus 500 and/or the intervertebral cage 100, 300.

As depicted in FIG. 8, the deployment cable 806 comprises a first end 808 and a second end 810. In some embodiments, the first end 808 can comprise an attachment feature 812. The attachment feature 812 can be any feature configured to allow the attachment of the deployment cable 806 to a portion of the intervertebral cage 100, 300 and/or to prevent the movement of the deployment cable 806 in one or several specified directions relative to the intervertebral cage 100, 300.

The attachment feature 812 can comprise a variety of shapes and sizes and can be made from a variety of materials. In one embodiment, for example, the attachment feature 812 can comprise a shape and/or size that allows the attachment feature 812 to engage a portion of the intervertebral cage 100, 300 and thereby restrict the movement of the deployment cable 806 relative to the intervertebral cage 100, 300. As specifically seen in FIG. 8, in some embodiments, the attachment feature can comprise a spherical feature located at the first end 808 of the deployment cable 806.

In some embodiments, the deployment cable 806 can comprise a breakage point (not shown). In some embodiments, the breakage point can be a portion of the deployment cable 806 that is configured to sever, break, and/or separate when a force threshold is exceeded. In some embodiments, the force threshold for the breakage point can be below the force threshold that would cause other portions and/or features such as, for example, the attachment feature 812 and/or the locking feature 814 of the deployment cable 806 to break or fail. In some embodiments, the breakage point can be positioned between, for example, between the locking feature 814 and the second end 810 of the deployment cable 806. Advantageously, as the application of a force above the force threshold results in the breakage of the deployment cable 806 at the breakage point, such positioning of the breakage point can eliminate the need to cut the deployment cable 806 after the intervertebral cage 100, 300 has been deployed.

As also seen in FIG. 8, the second end 810 of the deployment cable 806 can be connected to a portion of the deployment tool 802. As further seen in FIG. 8, in some embodiments, the deployment cable 806 further comprises a locking feature 814 that can be, for example, located at any position along the deployment cable, and in some embodiments, located between the attachment feature 812 and the second end 810 of the deployment cable 806. The locking feature 814 can be configured to allow a user to lock and/or secure the intervertebral cage 100, 300 in a deployed configuration. In some embodiments, the locking feature 814 can comprise the size and/or shape configured to interact with a portion of the intervertebral cage 100, 300 and thereby prevent the intervertebral cage 100, 300 from returning to an undeployed configuration after the intervertebral cage 100, 300 has been deployed.

In some embodiments, for example, the distance between the attachment feature 812 and the locking feature 814 can vary. Specifically, for example, the distance between the attachment feature 812 and the locking feature 814 can vary based on the size of the intervertebral cage 100, 300, the distance that the deployment cable 806 must be moved before the intervertebral cage 100, 300 deploys, and/or any other desired parameters.

Figure 9:
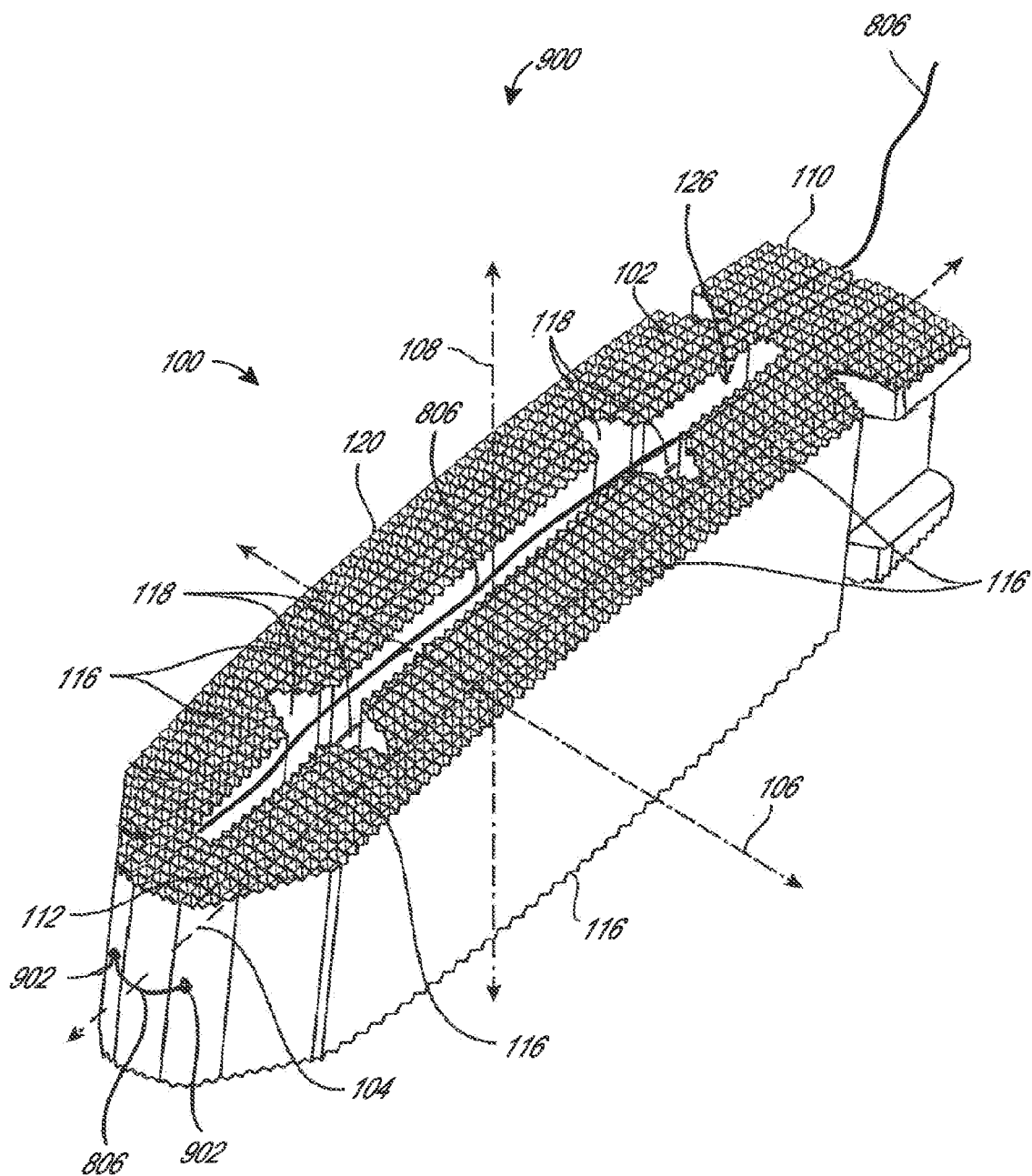
FIG. 9 is a perspective view of one embodiment of an intervertebral cage apparatus including an intervertebral cage and a deployment cable in an undeployed configuration.
Figure 10A:
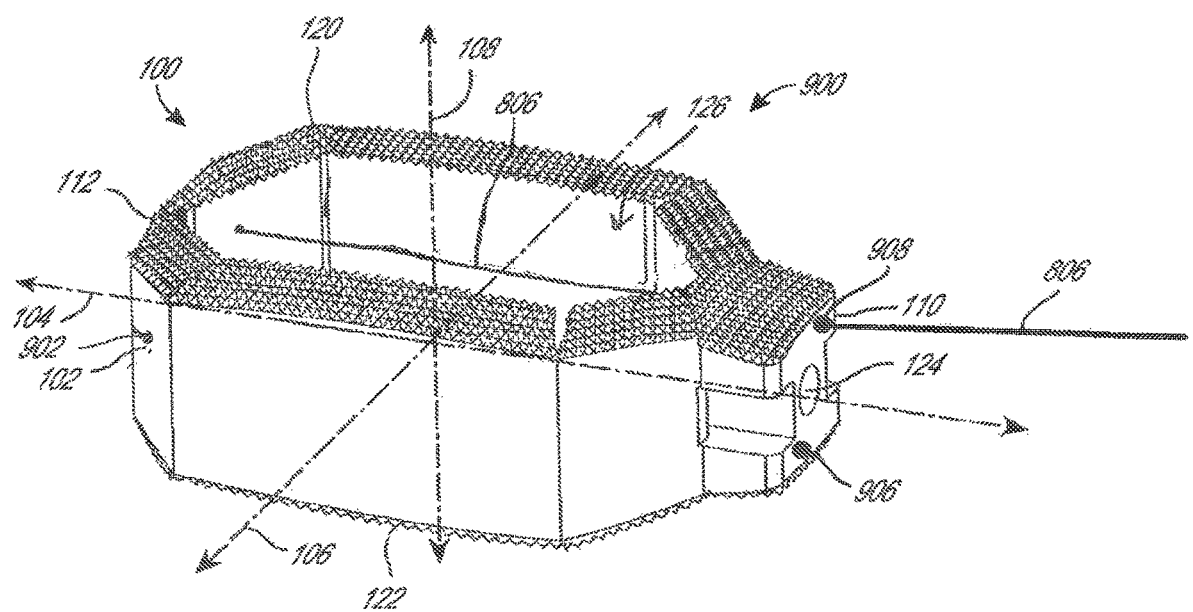
FIG. 10A is a perspective view of one embodiment of an intervertebral cage apparatus including an intervertebral cage and a deployment cable in a deployed configuration.
Figure 10B:
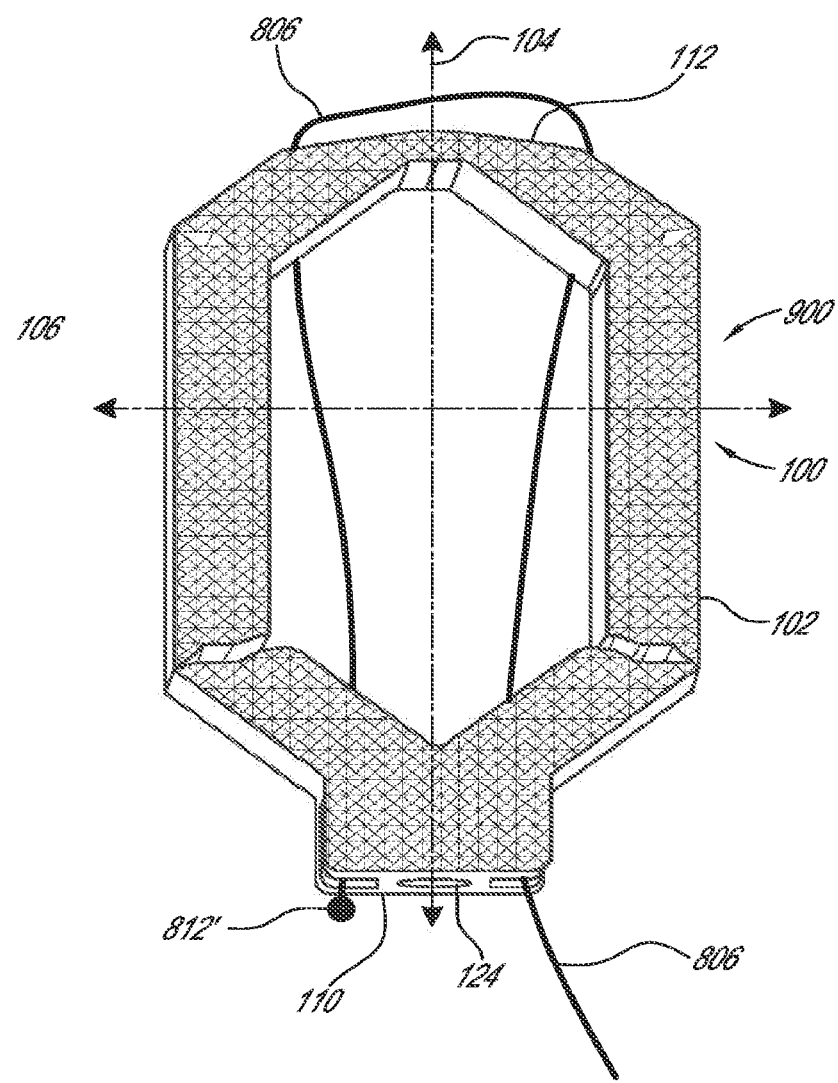
FIG. 10B is a top view of one embodiment of an intervertebral cage apparatus including an intervertebral cage and a deployment cable in a deployed configuration.

FIGS. 9 and 10 depict perspective views of one embodiment of an intervertebral cage apparatus 900. Specifically, FIG. 9 depicts one embodiment of the intervertebral cage apparatus 900 in an undeployed configuration and FIG. 10 depicts a perspective view of one embodiment of an intervertebral cage apparatus 900 in a deployed configuration. As seen in FIGS. 9 and 10, the intervertebral cage 100 can be configured for use with a deployment cable 806. In some embodiments, for example, the intervertebral cage 100 can comprises one or several opening and/or one or several channels configured to receive, direct, and/or hold a portion of the deployment cable. These openings can comprise a variety of shapes and sizes, and can be located on any desired portion of the intervertebral cage. In some embodiments, the size and shape of the openings can be determined by the size and shape of features accommodated by the openings, such as, for example, the deployment cable 806, the attachment feature 812, and/or the locking feature 814. Specifically, for example, the intervertebral cage 100 can comprise one or several distal openings 902 located proximate to the distal end 112 of the body 102 of the intervertebral cage 100 and a first and/or second proximal opening 906, 908 located proximate to the proximal end 110 of the intervertebral cage 100.

The distal opening(s) 902, the first proximal opening 906, and the second proximal opening 908 can be configured to receive a portion of the deployment cable 806. In some embodiments, for example, all or some of the distal opening(s) 902, the first proximal opening 906 and/or the second proximal opening 908 can guide the deployment cable 806 into and out of a portion of the intervertebral cage 100. In some embodiments, these openings 902, 906, 908 can be connected to one or several channels that pass through all or portions of the intervertebral cage 100. Thus, in some embodiments, the deployment cable may enter into the intervertebral cage 100 through the first proximal opening 906, and after passing through all or a portion of the intervertebral cage 100, the deployment cable 806 may then exit the channel inside the intervertebral cage 100 via another opening such as, for example, the distal opening 902 and/or the second proximal opening 908.

As further seen in FIG. 9, in some embodiments, the deployment cable 806 can pass through the internal volume 126 of the body 102 of the intervertebral cage 100. Specifically, in some embodiments, all or portions of the deployment cable 806 can extend from a first proximal opening 906 to a distal opening 902 and/or from a distal opening 902 to a second proximal opening 908 alongside an inner surface of the cage 100.

In some embodiments, a plurality of deployment cables 806 can be used in connection with a single intervertebral cage 100, 300. In some embodiments, the number of deployment cables 806 can be determined by the desired type of deployment. Thus, in some embodiments, the more deployment cables 806 may be used to achieve a more complex deployment motion.

Figure 11:
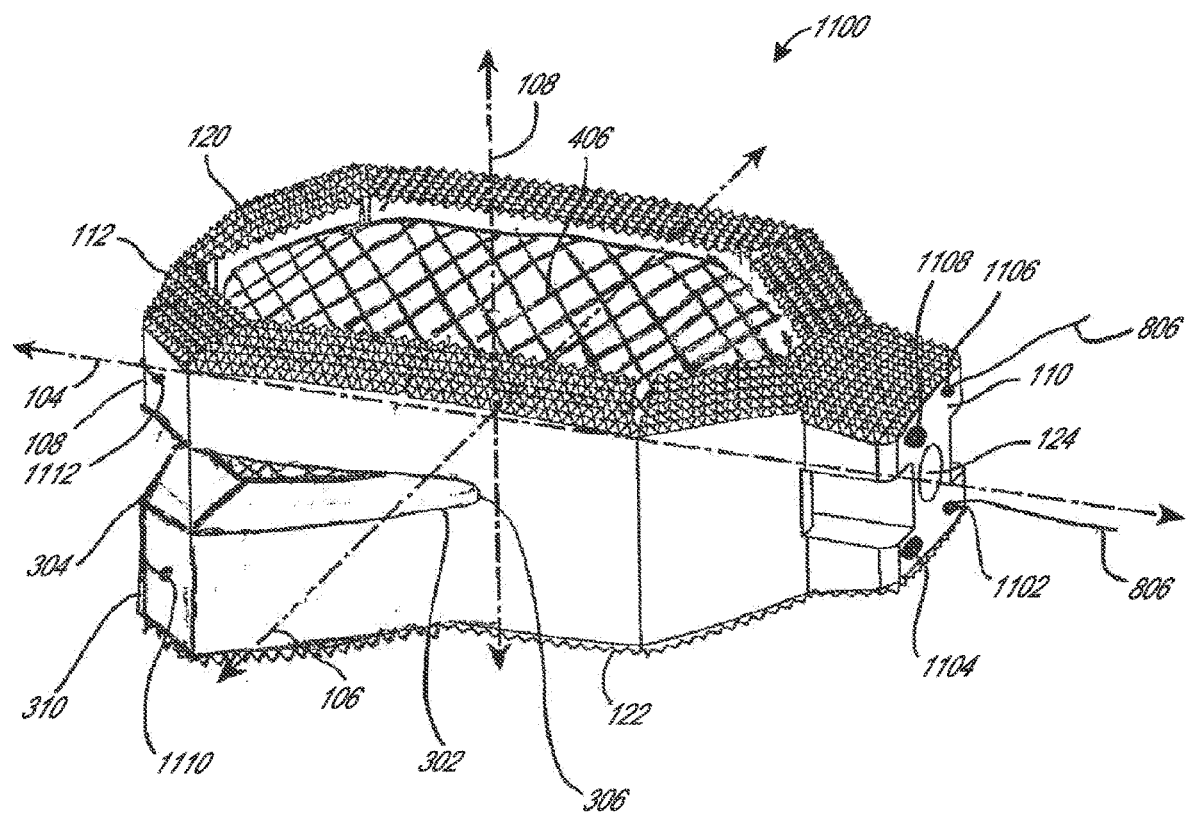
FIG. 11 is a perspective view of one embodiment of an intervertebral cage apparatus including a variable volume pouch, a deployment cable, and an intervertebral cage having a lateral split in a deployed configuration.

FIG. 11 depicts one embodiment using a plurality of deployment cables. Specifically, FIG. 11 depicts a further embodiment of the intervertebral cage apparatus 1100. As seen in FIG. 11, the intervertebral cage apparatus 1100 comprises the intervertebral cage 300 comprising a lateral split 302. As further seen in FIG. 11, the intervertebral cage 300 further comprises a lower first proximal opening 1102, a lower second proximal opening 1104, an upper first proximal opening 1106, an upper second proximal opening 1108, a lower distal opening 1110, and an upper distal opening 1112.

As also seen in FIG. 11, the intervertebral cage apparatus 1100 comprises two deployment cables 806. One of the deployment cables 806 depicted in FIG. 11 inserts through the lower first proximal opening 1102 and then passes through the variable volume pouch 400 where it exits through one of at least one lower distal opening 1110 before again passing through the variable volume pouch and to the lower second proximal opening 1104. This path of the deployment cable 806 secures a portion of the variable volume pouch 400 to the intervertebral cage 300 and specifically to the bottom portion 310 of the intervertebral cage 300.

As also seen in FIG. 11, the other deployment cable 806 passes through the upper first proximal opening 1106 and then through the variable volume pouch to at least one of the upper distal openings 1112 before again passing through the variable volume pouch and to the upper second proximal opening 1108. Similar to the deployment cable 806 passing through the lower openings 1102, 1104, 1110, the deployment cable 806 passing through the upper openings 1106, 1108, 1112, secures a portion of the variable volume pouch 400 to the intervertebral cage 300 and specifically to the top portion 308 of the intervertebral cage 300. Advantageously, the securement of the variable volume pouch 400 to the top portion 308 and the bottom portion 310 allows use of a variable volume pouch 400 to at least partially vertically deploy the intervertebral cage 300 with respect to the vertical axis 108 by filling the internal portion of the variable volume pouch 400.

While FIG. 11 depicts an embodiment in which two deployment cables 806 are used and showing specific positions for the openings 1102, 1104, 1106, 1108, 1110, 1112, a person of skill in the art will recognize that any number of deployment cables 806 can be used in connection with the intervertebral cage 300 and that a wide variety of positions for the openings can be used.

Methods of Using an Intervertebral Cage Apparatus

Figure 12:
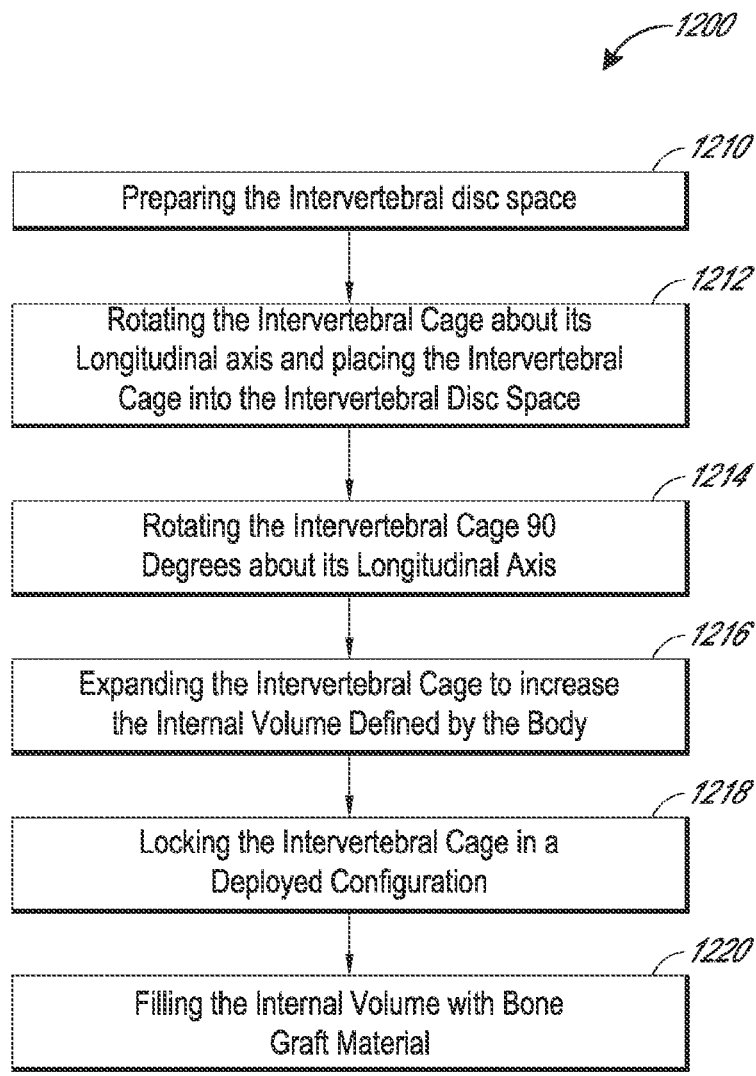
FIG. 12 is a flowchart illustrating one embodiment of process for using the intervertebral cage and/or the intervertebral cage apparatus.

FIG. 12 is a flowchart illustrating one embodiment of process 1200 for using the intervertebral cage 100, 300 and/or the intervertebral cage apparatus 500, 1100. The process begins at block 1210 wherein the intervertebral disc space is prepared, for example, by removing a portion of the annulus, evacuating the nucleus, and then removing the cartilaginous endplates.

After the intervertebral disc space is prepared, the process 1200 proceeds to block 1212 wherein the intervertebral cage 100, 300 is placed into the intervertebral disc space. In one embodiment, the intervertebral cage 100, 300 is rotated about its longitudinal axis 104 and placed in the intervertebral disc space such that the vertical axis 108 of the body 102 of the intervertebral cage 100, 300 is parallel to the vertebral endplates.

The process 1200 proceeds to block 1214 wherein the intervertebral cage 100, 300 is rotated 90 degrees about its longitudinal axis 104. After the rotation of the intervertebral cage 100, 300, the top 120 and the bottom 122 contact the vertebral endplates. In some embodiments, in which the distance between the top 120 and the bottom 122 of the body 102 of the intervertebral cage 100, 300 is larger than the width of the body 102 of the intervertebral cage 100, 300 as measured parallel to the lateral axis 106, the 90 degree rotation of the body 102 along its longitudinal axis 104 increases the height of the intervertebral disc space.

Figure 14:
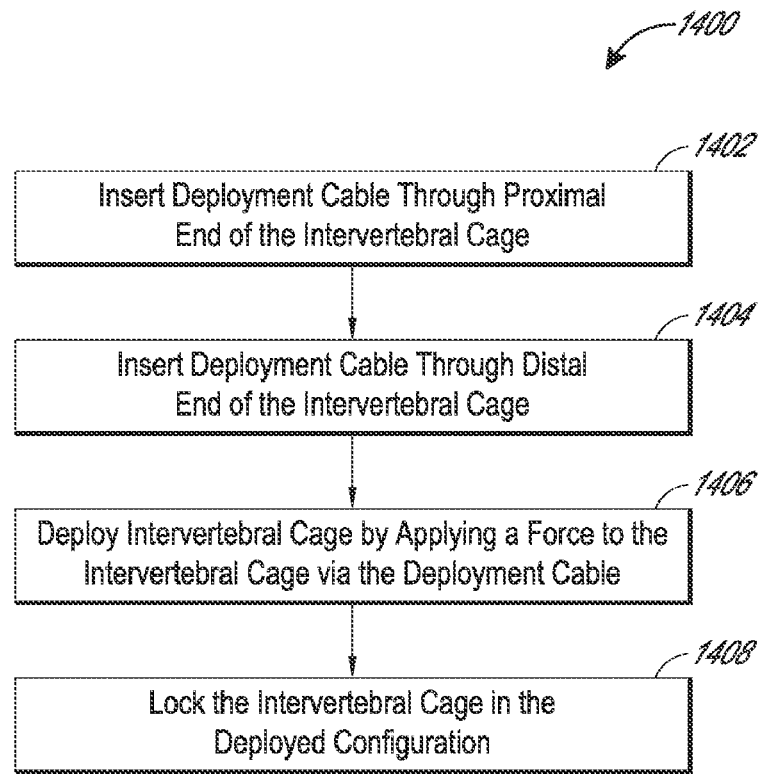
FIG. 14 is a flowchart illustrating one embodiment of a method of using an intervertebral cage apparatus including an intervertebral cage and a deployment cable.

After the intervertebral cage 100, 300 is rotated 90 degrees about its longitudinal axis 104, the process 1200 proceeds to block 1216 wherein the intervertebral cage 100, 300 is expanded to increase the internal volume 126 defined by the body 102, and in some embodiments, defined by the segments 116 and flexible connectors 118 forming the body 102. In some embodiments, the expansion of the intervertebral cage 100, 300 can proceed as outlined in step 1406 as depicted in FIG. 14.

In some embodiments, the body 102 is expanded until the body 102 attains a deployed configuration. In some embodiments, for example, in which a the intervertebral cage 100, 300 is used in connection with a deployment tool 802, the actuation of the deployment tool 802 can cause the deployment of the intervertebral cage 100, 300 and thereby the expansion of the intervertebral cage 100, 300 and the expansion of the internal volume 126 of the intervertebral cage 100, 300. In some embodiments in which the intervertebral cage 100, 300 comprises a body 102 made of a memory material such as, for example, PEEK Altera™, the intervertebral cage 100, 300 can be deployed by triggering the memory material such that the intervertebral cage 100, 300 transforms from the undeployed, second position to the deployed, first position. In some embodiments, triggering can be temperature induced, stress induced, electrically and/or mechanically induced, chemically induced, and/or through any other triggering mechanism. In some specific embodiments, the triggering can be induced when a threshold temperature of the intervertebral cage 100, 300 is exceeded, or when a stress threshold for the intervertebral cage 100, 300 is surpassed.

After the intervertebral device is expanded to increase the internal volume 126 defined by the body 102, the process 1200 can, in some embodiments, proceed to block 1218 wherein the intervertebral device is locked in a deployed configuration with a locking mechanism such as, for example, a deployment cable 806. Although the process 1200 can, in some embodiments, include block 1218, the steps of this block can be omitted and the process 1200 can proceed to block 1220.

The process 1200 can then proceed to block 1220, wherein the internal volume 126 of the body 102 of the intervertebral cage 100, 300 is filled with bone graft material to permit bone fusion between adjacent vertebrae. In some embodiments, the internal volume 126 of the body 102 of the intervertebral cage 100, 300 can be filled via the proximal aperture 124 located in the proximal end 110 of the body 102 of the intervertebral cage 100, 300.

A person of skill in the art will recognize that the steps of the aforementioned process can be performed in the same order, or in a different order. A person of skill in the art will further recognize that the process 1200 can include more or fewer steps than those outlined above.

Figure 13:
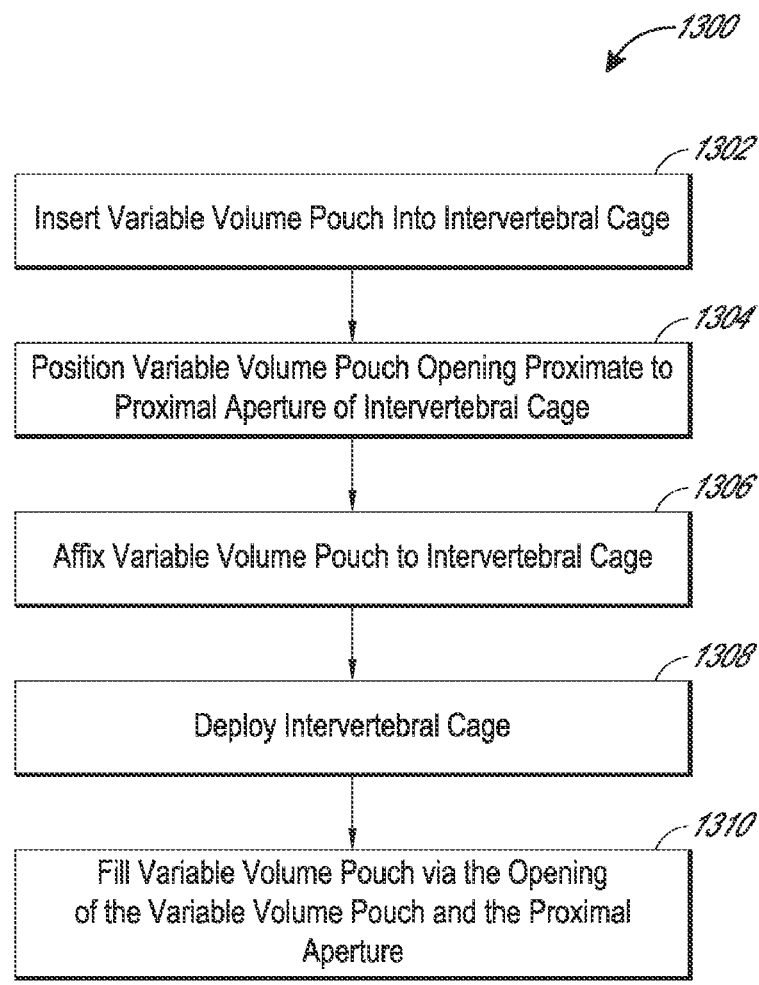
FIG. 13 is a flowchart illustrating one embodiment of a method of using a variable volume pouch and an intervertebral cage as part of an intervertebral cage apparatus.

FIG. 13 is a flow chart illustrating one embodiment of the process 1300 for using an intervertebral cage apparatus 500. In some embodiments, parts of the process 1300 can be performed before insertion of the intervertebral cage apparatus 500 into an intervertebral space, and in some embodiments, parts of the process 1300 can be performed after insertion of the intervertebral cage apparatus into an intervertebral space.

The process 1300 begins at block 1302 wherein the variable volume pouch 400 is inserted into the intervertebral cage 100, 300. In some embodiments, for example, the insertion of the variable volume pouch 400 into the intervertebral cage 100, 300 can be performed using a variety of tools and techniques. In some embodiments, for example, the variable volume pouch can be inserted into the intervertebral cage 100, 300 via the proximal aperture 124 in the proximal end 110 of the body 102 of the intervertebral cage 100, 300. In some embodiments, the variable volume pouch 400 can be inserted into the internal volume 126 of the intervertebral cage 100, 300 via the proximal aperture 124 located in the proximal end 110 of the intervertebral cage 100, 300. In some embodiments, the variable volume pouch 400 can be pre-inserted into the intervertebral cage 100, 300, and the process 1300 can begin at a block other than block 1302.

After the variable volume pouch 400 has been inserted into the intervertebral cage 100, 300, the process 1300 then proceeds to block 1304 wherein the opening 406 of the variable volume pouch 400 is positioned proximate to the proximal aperture 124 of the intervertebral cage 100, 300. In some embodiments, the positioning of the opening 406 of the variable volume pouch 400 proximate to the proximal aperture 124 of the intervertebral cage 100, 300 can be achieved, for example, by inserting the second end 404 of the variable volume pouch 400 through the proximal aperture 124 before inserting the first end 402 of the variable volume pouch 400 through the proximal aperture 124. By following this insertion procedure, and thereby inserting the second end 404 of the variable volume pouch 400 through the proximal aperture 124 first, the opening 406 of the variable volume pouch 400 which is located at the first end 402 of the variable volume pouch 400 can be easily positioned proximate to the proximal aperture 124 of the intervertebral cage 100, 300. In some embodiments in which the variable volume pouch 400 is pre-inserted into the intervertebral cage 100, 300, the process 1300 can begin at block 1304. In some embodiments, the opening 406 of the variable volume pouch 400 can be pre-positioned proximate to the proximal aperture 124 of the intervertebral cage 100, 300, and the process 1300 can begin at a block other than block 1304.

After the opening 406 of the variable volume pouch 400 has been positioned proximate to the proximal aperture 124 of the intervertebral cage 100, 300, the process 1300 proceeds to block 1306 wherein the variable volume pouch 400 is affixed to the intervertebral cage 100, 300. In some embodiments, for example, the variable volume pouch 400 can be affixed to all or portions of the intervertebral cage 100, 300 and specifically to all or portions of the body 102 of the intervertebral cage 100, 300. In some embodiments, for example, the variable volume pouch 400 can be affixed to the body 102 of the intervertebral cage 100, 300 along the portions of the body 102 defining the internal volume 126. Specifically, portions of the variable volume pouch 400 can be affixed to the segments 116 and flexible connectors 118 that constitute the body 102.

In some embodiments, the variable volume pouch 400 can be affixed to the body 102 of the intervertebral cage 100, 300 with features located on the body 102 of the intervertebral cage 100, 300 such as, for example, one or several fasteners, one or several hooks, one or several snaps, one or several adhesive regions, and/or any other desired feature located on either or both of the variable volume pouch 400 and the body 102 of the intervertebral cage 100, 300. In some embodiments, for example, the variable volume pouch 400 can be affixed to the intervertebral cage 100, 300 through additional features that are not an integral part of either the variable volume pouch 400 or the body 102 of the intervertebral cage 100, 300. In some embodiments, these features can include, for example, one or several deployment cables 806. In some embodiments, for example, the deployment cable 806 can be fused to affix the variable volume pouch 400 to the intervertebral cage 100, 300. In some specific embodiments, the deployment cable 806 can be inserted through a portion of the intervertebral cage 100, 300 such as, for example, the body 102, be threaded through a portion of the variable volume pouch 400, and then again be inserted through a portion of the intervertebral cage 100, 300. In some embodiments, the passing of the deployment cable 806 through portions of the intervertebral cage 100, 300 and through portions of the variable volume pouch 400 can secure the variable volume pouch 400 to the intervertebral cage 100, 300.

In some embodiments, the variable volume pouch 400 can be connected to the intervertebral cage 100, 300 along the entire perimeter of the internal volume 126, and in some embodiments, the variable volume pouch 400 can be connected to the intervertebral cage 100, 300 at discrete points. In some embodiments, the variable volume pouch 400 can be connected to the intervertebral cage 100 at one point, two points, three points, four points, five points, six points, eight points, 10 points, 20 points, 50 points, or at any other or intermediate number of points. In some embodiments in which the variable volume pouch 400 is pre-inserted into the intervertebral cage 100, 300 and in which the opening 406 of the variable volume pouch 400 has been pre-positioned proximate to the proximal aperture 124 of the intervertebral cage 100, 300, the process 1300 can begin a block 1306. In some embodiments, the variable volume pouch 400 can be pre-affixed to the intervertebral cage 100, 300, and the process 1300 can begin at a block other than block 1306. In some embodiments in which the assembly of the intervertebral cage apparatus 500 is temporally separated from the use of the intervertebral cage apparatus 500, the process 1300 can terminate with block 1306.

In some embodiments of the process 1300 in which the assembly of the intervertebral cage apparatus 500 is temporally proximate to the use of the intervertebral cage apparatus 500, after the variable volume pouch 400 is affixed to the intervertebral cage 100, 300, the process 1300 can proceed to block 1308 wherein the intervertebral cage 100, 300 is deployed. In some embodiments, block 1308 can be preceded by processes for preparing the intervertebral space and for inserting the intervertebral cage apparatus 500. In some embodiments, these processes can include, for example, some or all of the steps of the process 1200 depicted in FIG. 12.

In some embodiments, the intervertebral cage 100, 300 can be deployed using any desired deployment technique and/or deployment device. In some specific embodiments, for example, the intervertebral cage can be deployed using a deployment system 800 comprising a deployment tool 802 and a deployment cable 806. In some embodiments, deployment of the intervertebral cage 100, 300 can result in a change in the dimensions of the intervertebral cage 100, 300 as measured along one or more of the longitudinal axis 104, the lateral axis 106, and/or the vertical axis 108.

After the intervertebral cage 100, 300 is deployed, the process 1300 proceeds to block 1310 wherein the variable volume pouch 400 is filled. In some embodiments, for example, the variable volume pouch 400 can be filled via the opening 406 at a variable volume pouch 400. In some embodiments, the variable volume pouch 400 can be filled via the opening 406 of the variable volume pouch and the proximal aperture 126 located in the proximal end 110 of the intervertebral cage 100, 300. In some embodiments, the variable volume pouch can be filled with, for example, a gaseous material, a liquid material, and/or a solid material. In some embodiments, the variable volume pouch 400 can be filled with a graph material which can comprise, for example, a solid material and specifically, a plurality of pieces of solid material. In some embodiments, these materials can comprise bone fragments and/or pieces of hones, and/or any biocompatible material.

In some embodiments, the variable volume pouch 400 can be filled with a desired amount of film material. In some embodiments, the desired amount of film material can be based on the desired size of the variable volume pouch 400 in its expanded state. Thus, in some embodiments, the desired size of the expanded state of the variable volume pouch 400 can determine the amount of film material. After the variable volume pouch 400 has been filled, steps can be taken to maintain the fill material within the variable volume pouch 400. In some embodiments, these steps can include, for example, scaling the opening 406, closing the opening 406, plugging the opening 406, or any other action that would prevent the film material from emptying out of the variable volume pouch 400.

FIG. 14 is a flowchart illustrating one embodiment of the process 1400 for preparing and/or using the intervertebral cage apparatus 900, 1100, which may or may not have a variable volume pouch 400. In some embodiments, the process 1400 can be performed before insertion of the intervertebral cage apparatus 900, 1100 into an intervertebral space, and in some embodiments, the process 1400 can be performed after insertion of the intervertebral cage apparatus into an intervertebral space.

The process 1400 begins at block 1402 wherein the deployment cable 806 is inserted through the proximal end 110 of the intervertebral cage 100, 300. In some embodiments, for example, the deployment cable 806 is inserted through the proximal end 110 of the intervertebral cage 100, 300 by inserting the deployment cable 806 through a first proximal opening 906, 1104, 1108. In some embodiments, the deployment cable 806 that is inserted through the first proximal opening 906, 1104, 1108 passes through the proximal end 110 of the intervertebral cage 100, 300 and into the internal volume 126 of the intervertebral cage 100, 300. In some embodiments, the deployment cable 806 that is inserted into the first proximal opening 906, 1104, 1108 passes into a channel and passes through all or portions of the intervertebral cage 100, 300. In some embodiments, the deployment cable 806 can be pre-inserted through the proximal end 110 of the intervertebral cage 100, 300, and the process 1400 can begin at a block other than block 1402. In some embodiments, the deployment cable 806 need not be inserted through the proximal end 110 of the intervertebral cage 100, 300, but is rather simply attached or affixed at or near the proximal end 110 of the intervertebral cage 100, 300.

After the deployment cable 806 is inserted through or affixed to the proximal end 110 of the intervertebral cage 100, 300, the process 1300 moves to block 1304 and the deployment cable 806 is inserted through the distal end 112 of the intervertebral cage 100, 300. In some embodiments, the deployment cable 806 can be inserted into the distal end 112 of the intervertebral cage 100, 300 by inserting the deployment cable 806 into and/or through a distal opening 902, 1110, 1112. In some embodiments, in which the deployment cable 806 passed through the proximal end 1110 of the intervertebral cage 100, 300 and into the internal volume 126, the deployment cable 806 can be inserted into the distal end 112 via the distal opening 902, 1110, 1112 from the internal volume 126. In some embodiments, in which the deployment cable 806 passes through a channel from the first proximal opening 906, 1104, 1108, the deployment cable 806 may be inserted through the distal end 1112 of the intervertebral cage 100, 300 by passing through a channel that travels through the distal end of the intervertebral cage. In some embodiments in which the deployment cable 806 has been pre-inserted through the proximal end 110 of the intervertebral cage 100, 300, the process 1400 can begin at block 1404. In some embodiments, the deployment cable 806 can be pre-inserted through the distal end 112 of the intervertebral cage 100, 300, and the process 1400 can begin at a block other than block 1404. In some embodiments in which the assembly of the intervertebral cage apparatus 900, 1100 is temporally separated from the use of the intervertebral cage apparatus 900, 1100, the process 1400 can terminate with block 1404.

In some embodiments, after the deployment cable 806 is inserted through the distal end 112 of the intervertebral cage 100, 300 the deployment cable 806 can be returned to the proximal end 110 of the intervertebral cage 100, 300. In some embodiments, the deployment cable 806 can return to the proximal end 110 of the intervertebral cage 100, 300 by inserting the deployment cable 806 into and/or through a second distal opening 902, 1110, 1112. After the deployment cable 806 has been inserted into and/or through the second distal opening 902, 1110, 1112, the deployment cable 806 passes through the distal end 112 of the intervertebral cage 100, 300 and into the internal volume 126 of the intervertebral cage 100, 300. In some embodiments, the deployment cable 806 that is inserted into the distal opening 902, 1110, 1112 passes into a channel and passes through all or portions of the intervertebral cage 100, 300.

After the deployment cable 806 returns to the proximal end 110 of the intervertebral cage 100, 300, the deployment cable 806 can be inserted through the proximal end 110 of the intervertebral cage 100, 300 by inserting the deployment cable 806 through a second proximal opening 908, 1102, 1106. In some embodiments, the deployment cable 806 that is inserted through the second proximal opening 908, 1102, 1106 passes from the internal volume 126 of the intervertebral cage 100, 300 and through the proximal end 110 of the intervertebral cage 100, 300. In some embodiments, the deployment cable 806 can be pre-inserted through the proximal end 110 of the intervertebral cage 100, 300. In some embodiments, the deployment cable 806 need not be inserted through the proximal end 110 of the intervertebral cage 100, 300, but can rather be simply attached or affixed at or near the proximal end 110 of the intervertebral cage 100, 300.

After the deployment cable 806 is inserted through or affixed to the proximal end 110 of the intervertebral cage 100, 300, the deployment cable 806 can be connected to the deployment tool 802, which can then be used to deploy the intervertebral cage 100, 300.

In some embodiments of the process 1400 in which the assembly of the intervertebral cage apparatus 900, 1100 is temporally proximate to the use of the intervertebral cage apparatus 900, 1100, the process 1400 proceeds to block 1406 wherein the intervertebral cage 100, 300 is deployed by applying a force to the intervertebral cage 100, 300 via the deployment cable 806. The force that is applied to the intervertebral cage 100, 300 via the deployment cable 806 can be generated using a variety of tools and/or techniques. In some embodiments, for example, in which the deployment cable 806 is part of an insertion system 800 including a deployment tool 802, the force can be applied to the intervertebral cage 100, 300 via the deployment cable 806 by using the control interface 804 to tension the deployment cable 806. In some embodiments, and as the force is applied to the intervertebral cage 100, 300 via the deployment cable 806, the user is provided feedback via the deployment tool 802 to allow the user to understand the status of the deployment. Specifically, in some embodiments, the deployment tool 802 can be configured to provide user feedback indicating that the further application of force to the intervertebral cage 100, 300 will result in the locking of the intervertebral cage 100, 300 in a deployed configuration. In some embodiments, for example, this feedback can comprise an audible, visual, and/or tactile signal that indicates that the intervertebral cage 100, 300 is nearing the locked and/or deployed configuration. In some embodiments, block 1406 can be preceded by processes for preparing the intervertebral space and for inserting the intervertebral cage apparatus 900, 1100. In some embodiments, these processes can include, for example, some or all of the steps of the process 1200 depicted in FIG. 12.

After the intervertebral cage 100, 300 is deployed by applying a force to the intervertebral cage 100, 300 via the deployment cable 806, the process 1400 proceeds to block 1408 wherein the intervertebral cage 100, 300 is locked in the deployed configuration. In some embodiments, in which the deployment cable 806 includes a locking feature 814, the intervertebral cage 100, 300 can be locked into the deployed configuration through the use of the locking feature 814 on the deployment cable 806. In one specific embodiment of how the locking feature 814 could be used in connection with the intervertebral cage 100, 300 to lock the intervertebral cage 100, 300 into a deployed configuration, the locking feature can comprise a member having a dimension and/or diameter larger than the diameter of the deployment cable 806. As the deployment cable 806 is retracted from the second proximal opening 908, 1104, 1108 to deploy the intervertebral cage 100, 300 the locking feature 814 can be moved through the proximal end 110 of the intervertebral cage 100, 300 and out the second proximal opening 908, 1104, 1108. In some embodiments, in which a locking feature 814 is used to secure the intervertebral cage 100, 300 in a deployed and/or locked configuration, the second proximal opening 908, 1104, 1108 can be configured to allow the locking feature 814 to pass through the proximal end 110 of the intervertebral cage 100, 300 and out the second proximal opening 908, 1104, 1108 but to prevent the locking feature 814 from retracting through the second proximal opening 908, 1104, 1108 and back into the proximal end 110 of the intervertebral cage 100, 300. Thus, in some embodiments, once the locking feature has been withdrawn from the proximal end 110 of the intervertebral cage 100, 300, via the second proximal opening 908, 1104, 1108, the locking feature can engage with portions of the second proximal opening 908, 1104, 1108 to secure the intervertebral cage 100, 300 in a locked and/or deployed configuration. In some embodiments, after the intervertebral cage 100, 300 has been locked in the deployed configuration, the force threshold can be exceeded, and the deployment cable 806 can break at the breakage point. In some embodiments, after the intervertebral cage 100, 300 is in the locked and/or deployed configuration, fill and/or graft material can be inserted into the internal volume 126 of the body 102 of the intervertebral cage 100, 300 via the proximal aperture 124.

A person of skill in the art will recognize that the process 1300 and 1400 can include more or fewer steps than those outlined above. A person of skill in the art will further recognize that the above outlined steps of processes 1300 and 1400 can be performed in any desired order, and can include substeps or subprocesses. A person of skill in the art will further recognize that the specific methods of locking the intervertebral cage 100, 300 into a deployed configuration are not limited to the specific embodiments enumerated herein, but that a wide variety of techniques and devices can be used to lock the intervertebral cage 100, 300 in a deployed and/or locked configuration. A person of skill in the art will further recognize that the processes depicted in FIGS. 12, 13, and 14 can be combined, and that thus an intervertebral cage 100, 300 can be used with both the variable volume pouch 400 and the deployment cable 806.

Figure 15A:
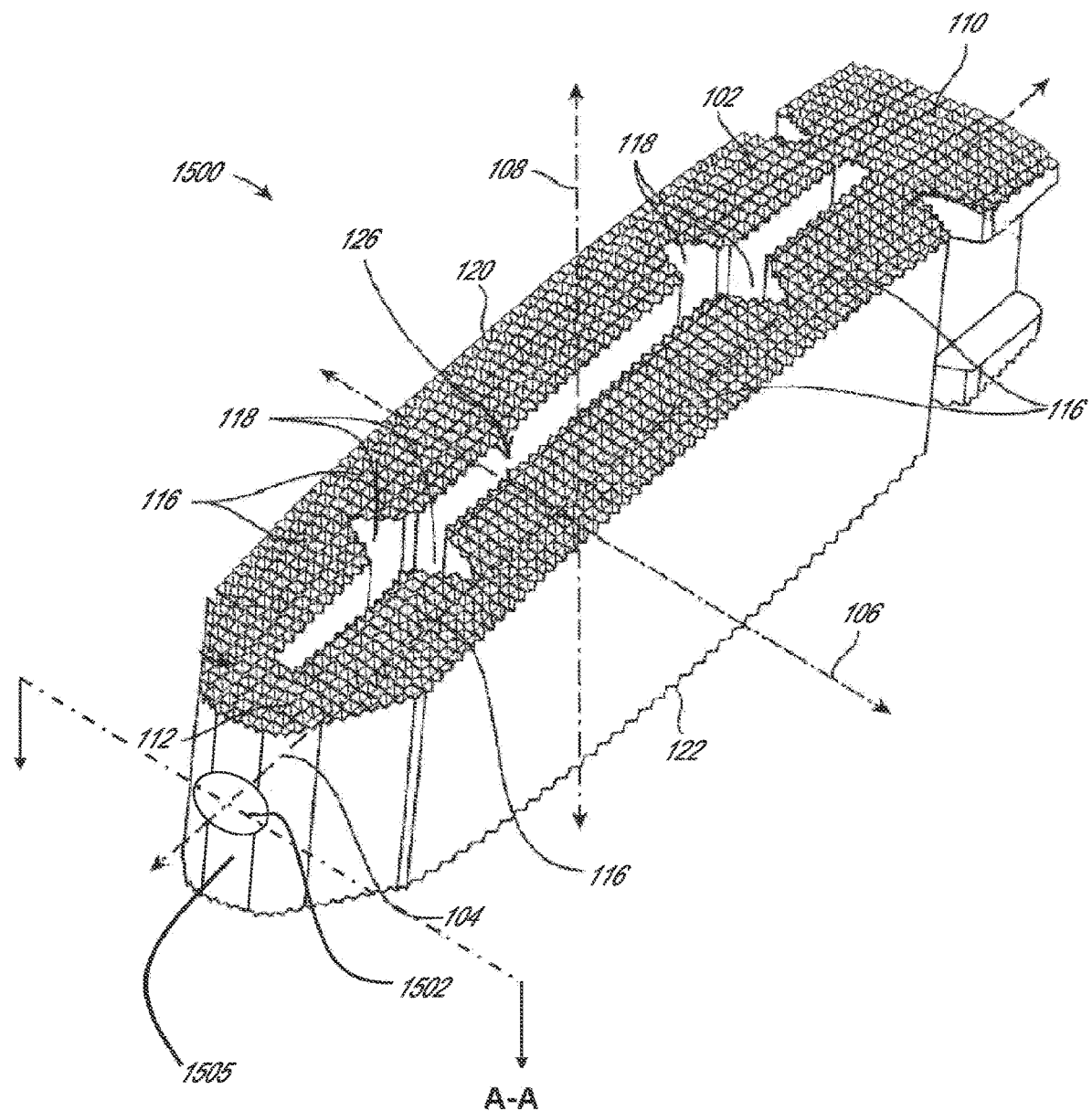
FIG. 15A is a perspective view of one embodiment of an intervertebral cage apparatus having a distal aperture in an undeployed position.
Figure 15B:
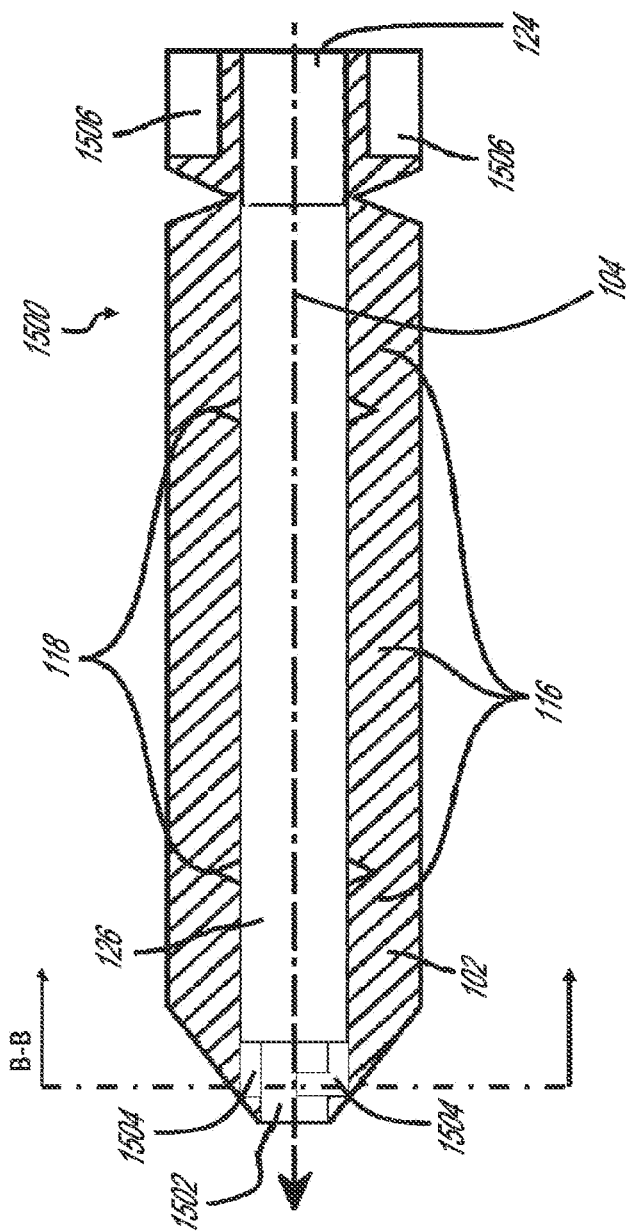
FIG. 15B is a cross-sectional view of one embodiment of an intervertebral cage apparatus along section A-A as shown in FIG. 15A.
Figure 15C:
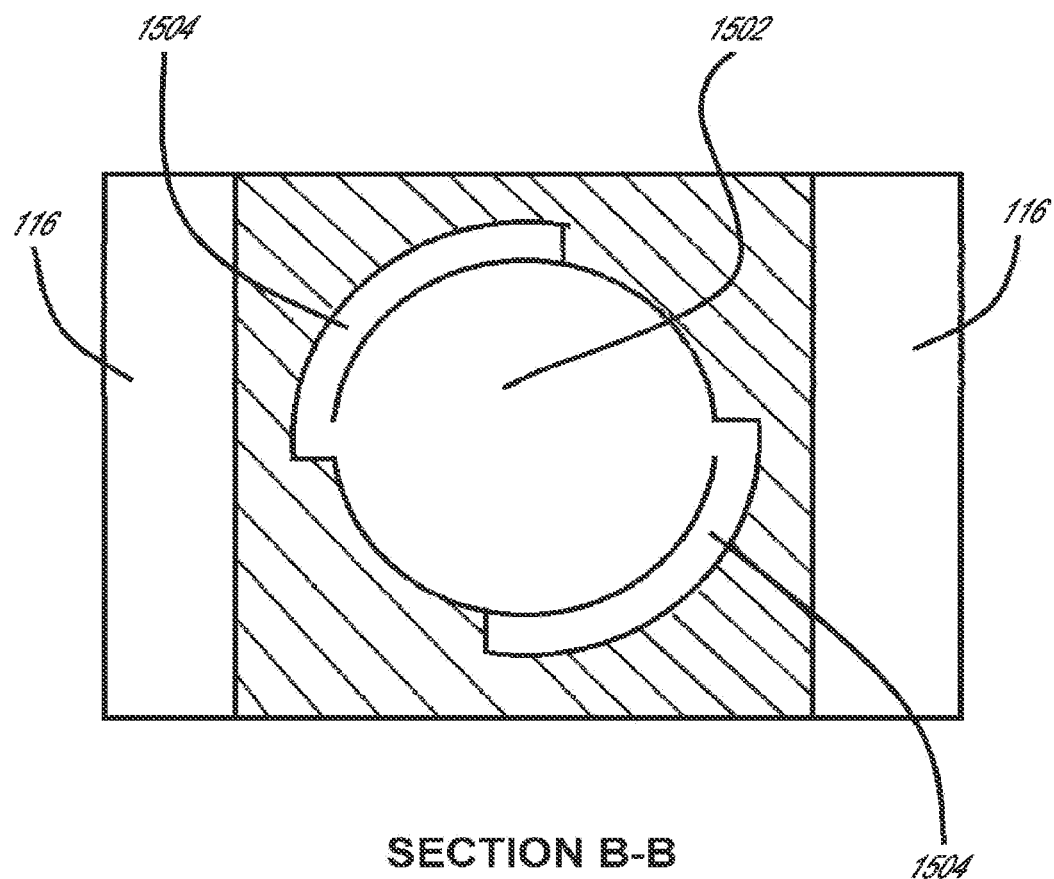
FIG. 15C is a cross-sectional view of one embodiment of an intervertebral cage apparatus along section B-B as shown in FIG. 15B showing a slot on a distal aperture.

FIGS. 15A-15C are illustrations of an embodiment of an intervertebral cage apparatus 1500 which has a distal aperture 1502 located at a distal end of the body 102. With reference to FIG. 15A which is a perspective view of the intervertebral cage apparatus 1500, the distal aperture 1502 is centered on the longitudinal axis 104 although in alternative embodiments the aperture 1502 may be offset from the axis 104. In the illustrated embodiment, the distal aperture 1502 has a diameter less than that of the proximal aperture 124 and incorporates a coupling mechanism along its inner surface. In certain embodiments, the coupling mechanism takes the form of a bayonet mount. As shown in FIG. 15B which is a cross-sectional view of the intervertebral cage apparatus 1500 along Section A-A (shown in FIG. 15A), the distal aperture may have two or more slots 1504 configured to receive two or more pins 1618 on a distal end of an implantation tool 1600 (described further with respect to FIGS. 16A-16C).

In the illustrated embodiment, the slots 1504 are "L-shaped" slots formed along the inner surface of the distal aperture such that a first portion of the slot extends from a proximal end of the distal aperture 1502 distally to a location between the proximal end and distal end of the aperture 1502. As shown more clearly in FIG. 15C which is a cross-sectional view of the intervertebral cage apparatus 1500 along Section B-B (shown in FIG. 15B), a second portion of the slot 1504 then extends radially along the inner circumference of the inner surface of the distal aperture. The radial extension can be about 45 degrees to about 135 degrees about the longitudinal axis 104. In the illustrated embodiment, the circumferential extension is about 90 degrees. In some embodiments, fewer or greater slots 1504 may be used. Additionally, in some embodiments, the slots 1504 may be placed such that the first portion of the slot 1504 is centered on a plane formed by axes 104 and 108. This could advantageously allow larger pins 1618 to be used (described further with respect to FIGS. 16A-16C) thereby reducing localized stresses and strains when deploying the device.

In other embodiments, slots 1504 of the distal aperture 1502 have no second portion such that the first portion runs entirely from a proximal end of the aperture 1502 to a distal end of the aperture 1502 allowing for the pins 1618 to wholly pass therethrough. In such embodiments, the pins 1618 of the implantation tool can instead be used to engage and abut a distal face 1505 of the intervertebral cage apparatus 1500. In yet other embodiments, the distal aperture 1502 has a diameter which is equal to, or greater than, the diameter of the proximal aperture 124. Furthermore, it is contemplated that in other embodiments, other types of coupling mechanisms may be used to couple the implantation device with the body 102, such as, but not limited to, a press fit, an interference fit, a friction fit, threads, and other coupling mechanisms known in the art.

Figure 16A:
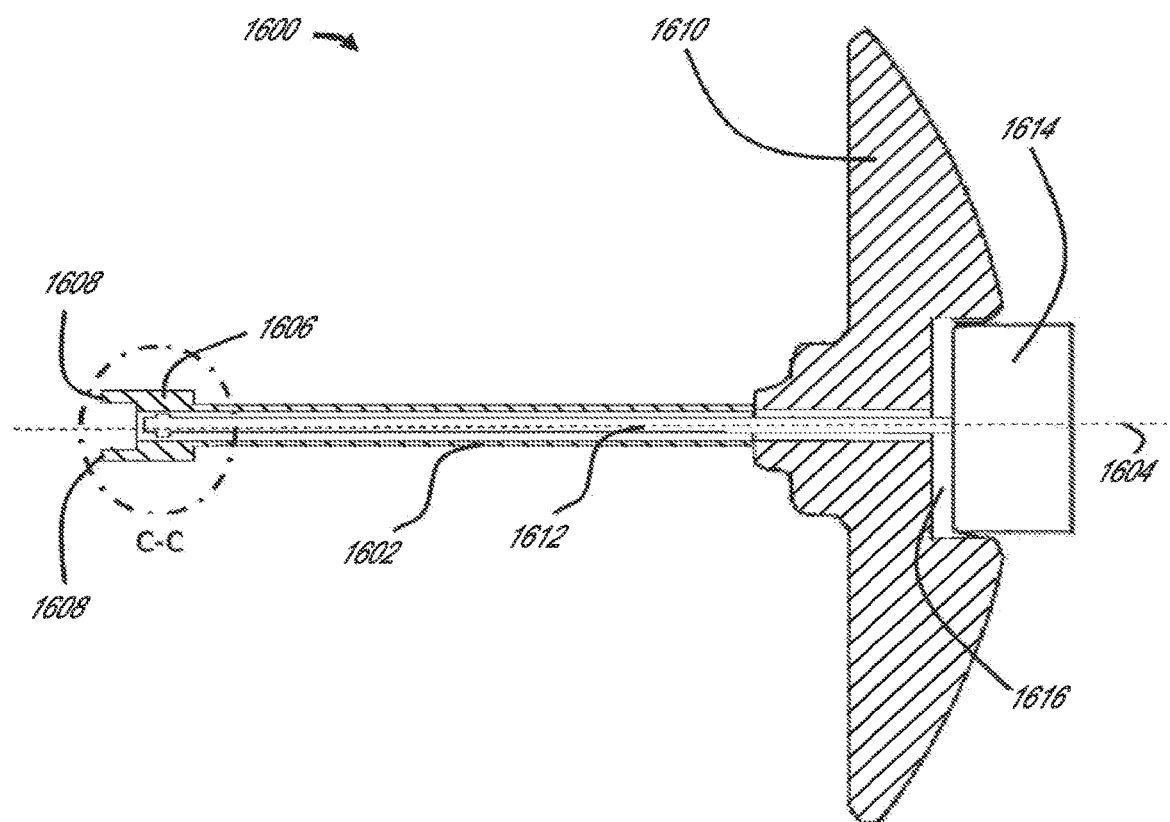
FIG. 16A is a partial cross-sectional view of one embodiment of an implantation tool which can be used to convert an intervertebral cage apparatus from an undeployed position to a deployed position.
Figure 16B:
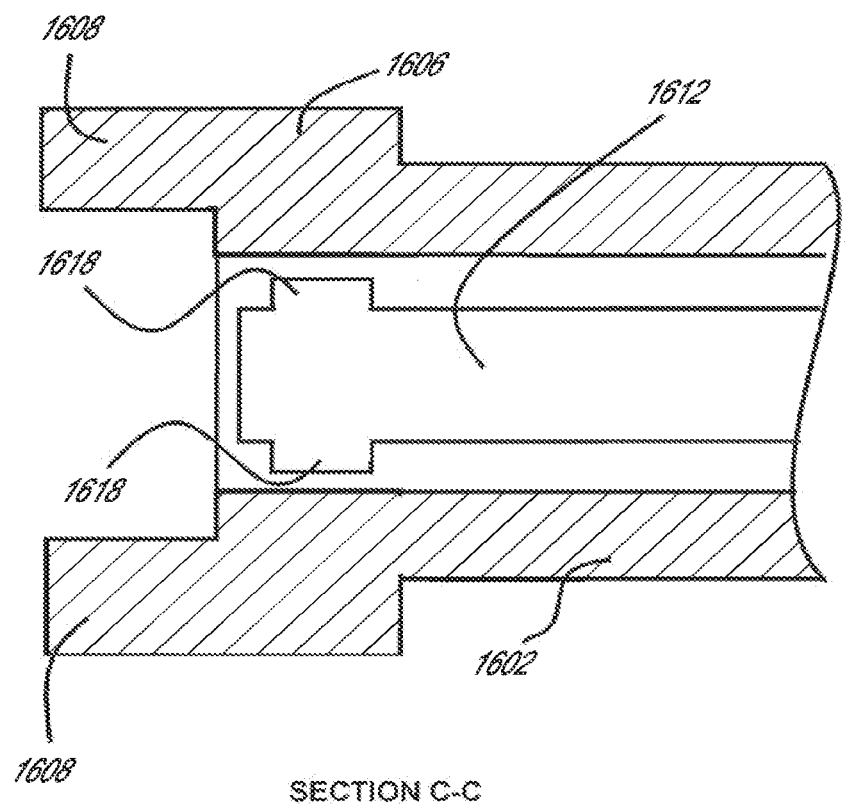
FIG. 16B is an enlarged view of a distal end of one embodiment of an implantation tool focused on Section A-A as shown in FIG. 16A.
Figure 16C:
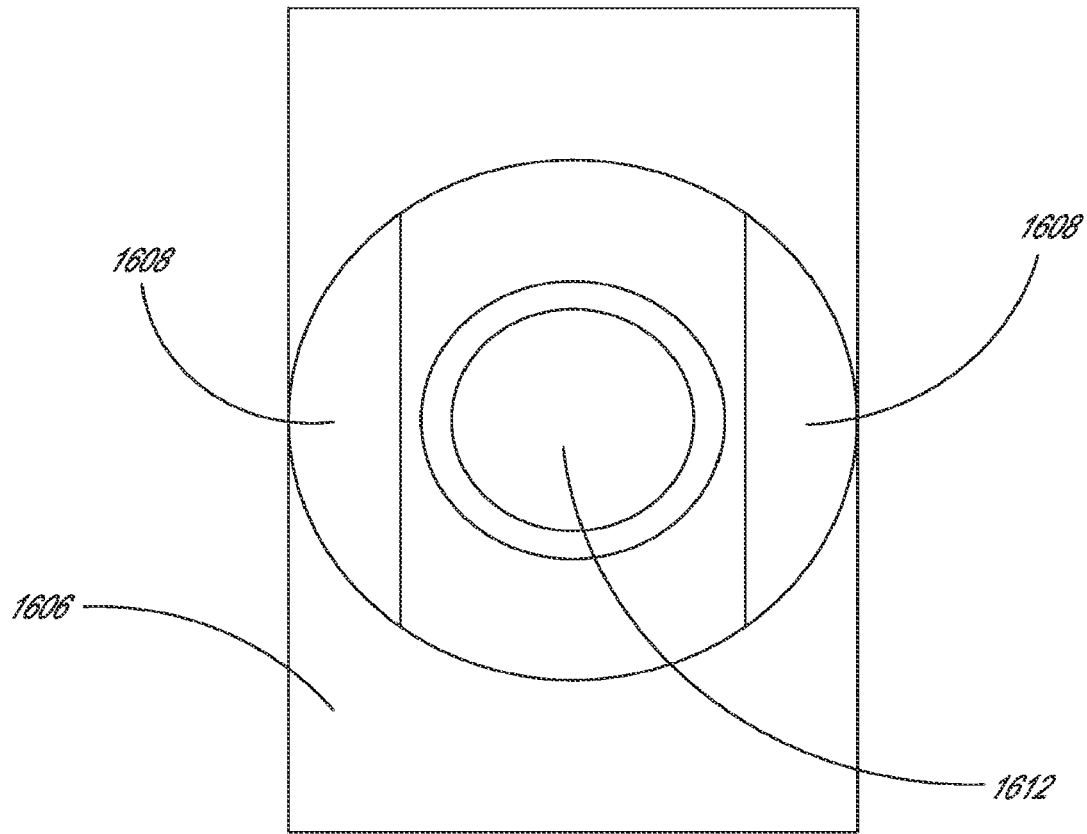
FIG. 16C is a view from the distal end of one embodiment of an implantation tool showing the distal end of an intervertebral cage apparatus having a connector, teeth, and shaft.

With reference to FIG. 15B, the proximal end 110 of the body 102 has cutouts 1506 configured to receive mating portions 1608 of an implantation tool 1600 shown in FIGS. 16A-16C. In the illustrated embodiment, two cutouts 1506 are located along the outer perimeter of the proximal end 110. In other embodiments, a different number of cutouts 1506 can be used and is not limited to placement along the outer perimeter of the proximal end 110 of the body 102.

FIGS. 16A-16C are illustrations of an embodiment of an implantation tool 1600 which can be used to convert the intervertebral cage apparatus 1500 or other cage apparatuses described herein from an undeployed position to a deployed position. With reference to FIG. 16A which is a partial cross-section of an embodiment of an implantation tool 1600, the implantation tool 1600 has an outer cannula 1602 extending between a proximal end and a distal end of the tool 1600 and centered on luminary axis 1604. At the distal end of outer cannula 1602 is a connector 1606 configured to contact the proximal end 110 of body 102. As shown more clearly in FIG. 16C, which is a view of the distal end of the implantation tool 1600, in one embodiment the connector 1606 has dimensions which are equal to, or greater than, the dimensions of the proximal end 110 of body 102 such that the connector 1606 advantageously distributes any contact pressure over the entire surface area of the proximal end 110. In some embodiments, connector 1606 has two mating portions 1608 such as teeth protruding distally from the connector 1606 which are configured to be inserted into and engage cutouts 1506 on the proximal end 110 of the body 102. In other embodiments, connector 1606 may have fewer or greater mating portions 1608 depending on the amount of cutouts 1506 on the proximal end 110 of the body 102. Once engaged, the mating portions 1608 are configured to directly link the rotation of the body 102 with the rotation of the outer cannula 1602 thereby providing a user of the implantation tool 1600 direct control of the rotation of the body 102 during an implantation procedure.

At the proximal end of the outer cannula 1602 is a handle 1610 configured to be held by a user of the implantation tool 1600. The handle 1610 is directly attached to the outer cannula 1602 such that rotation of the handle 1610 also causes rotation of the outer cannula 1602. As such, a user of the implantation tool 1600 can advantageously control the rotation of the body 102 through the handle 1610. Implantation tool 1600 also has an internal shaft 1612 centered about the luminal axis 1604 which is both slidably translatable and slidably rotatable within the outer cannula 1602. In the illustrated embodiment, the internal shaft 1612 is directly attached to control member 1614 such that rotation and translation of control member 1614 rotates and translates the internal shaft 1612. In this embodiment, the control member 1614 is wholly received within an aperture 1616 in the handle. In other embodiments, the aperture is sized only to receive the internal shaft 1612 such that the control member 1614 remains outside of the handle. Control member 1614 may have raised ridges, protrusions, texturing, grips, or other mechanisms to assist a user of the device to rotate and translate the control member 1614.

In some embodiments, at the distal end of shaft are pins 1618 which correspond to the coupling mechanism in the form of slots 1504 located on the distal aperture 1502 of the intervertebral cage apparatus 1500. Since shaft 1612 is slidably translatable and slidably rotatable within the outer cannula 1602, the shaft 1612 can be both be translated and rotated to engage the "L-shaped" slot 1504 of the distal aperture 1502 while a counter-force is applied to the body 102 via the outer cannula 1602 due to the engagement of the mating portions 1608 with the cutouts 1506.

Figure 17:
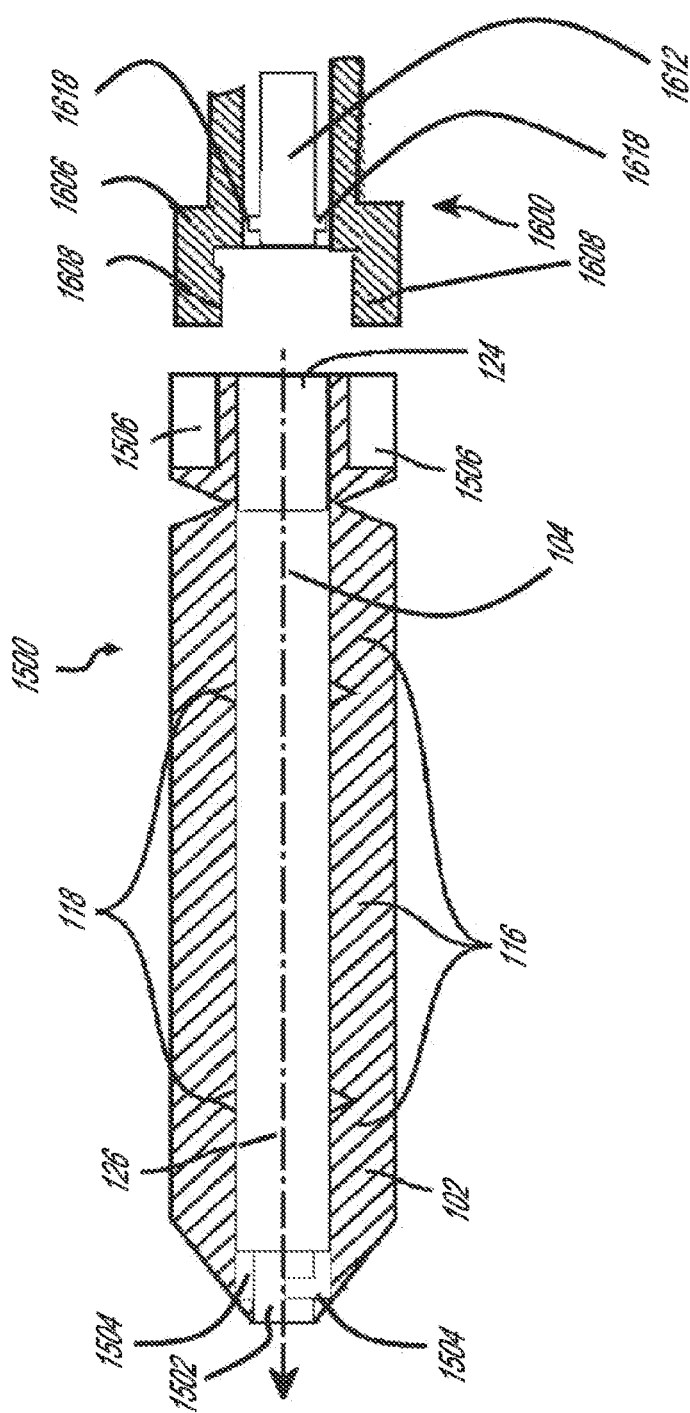
FIG. 17 is a cross-sectional view of one embodiment of the intervertebral cage apparatus having a distal aperture and one embodiment of an implantation tool prior to being connected.

FIG. 17 illustrates one method by which the implantation tool 1600 can be used to convert the intervertebral cage apparatus 1500 and any other such apparatus described herein from an undeployed position to a deployed position. In the illustrated embodiment, a shaft 1612 with pins 1618 and an intervertebral cage apparatus 1500 with a distal aperture 1502 containing slots 1504 is used. During a first step, the implantation tool 1600 is advanced towards the proximal end 110 of the intervertebral cage apparatus 1500 in the undeployed configuration such that the connector 1606 is placed adjacent to and in contact with the proximal end 110 of the body 102. During this advancement process, mating portions 1608 are simultaneously inserted into and engage the cutouts 1506 thereby linking the rotation of the body 102 with the rotation of the outer cannula 1602.

During a second step, the shaft 1612 is then slidingly advanced distally through the outer cannula 1602 and into the intervertebral cage apparatus 1500. The shaft advances first through the proximal aperture 124, then through the internal volume 126, and finally placed adjacent to and in contact with the trailing edge of the distal aperture 1502. In this embodiment, since the distal aperture 1502 has slots 1504 which correspond to the pins 1618 at the distal end of the shaft 1612, the shaft 1612 can be further advanced into the distal aperture 1502 by following the profile of the slot 1504. The shaft 1612 can then be rotated such that the shaft 1612 is engaged with the distal aperture 1502. In this engaged position, the shaft 1612 and body 102 are linked such that translation of the shaft 1612 results in translation of the body 1502. Note that the labeling of the above steps as "first" and "second" is used solely to describe one method of deploying the intervertebral cage apparatus 1500 and other cage apparatuses described herein. In other embodiments, this sequence can be reversed such that the second step is completed before the first step.

In embodiments of the intervertebral cage apparatus 1500 having slots 1504 which extend throughout the length of the distal aperture 1502, the shaft is advanced wholly through the distal aperture 1502. Upon the pins 1618 being distal the distal face 1505 of the body 102, the shaft 1612 is rotated and retracted such that the pins 1618 are abutting a distal face 1505.

Additionally, the above described steps can either be performed prior to or after insertion of the intervertebral cage apparatus 1500 into the intervertebral space. In embodiments where the above-described steps are performed prior to insertion into the intervertebral space, the implantation tool 1600 is used to deliver the device into the space. In embodiments where the above-described steps are performed after insertion into the intervertebral space, a separate tool may be used to deliver the device into the space.

During the third step, after the shaft 1612 has been engaged with the distal aperture 1502, a force is applied, in the distal direction, to the proximal end 110 of the body 102 while the shaft 1612 is held in place. The force applied to the proximal end 110 causes the body 102 to convert from the undeployed position to the deployed position due to deformation along flexible connectors 118. In an alternative embodiment, a force is applied, in the proximal direction, to the distal end of the body 102 at the distal aperture 1502 while the outer cannula 1602 is held in place to convert the body 102 from an undeployed position to a deployed position.

During the final step, the shaft 1612 is rotated to disengage pins 1618 from the "L-shaped" slot of the distal aperture 1502. The shaft 1612 is then slidingly retracted from the intervertebral cage apparatus 1500 such that the shaft 1612 is removed from the body 102. The connector 1606 may then be retracted such that the mating portions 1608 are removed from cutouts 1506. The tool may then be removed from the intervertebral space and the body of the patient.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein.

What is claimed is:

1. A method of deploying an intervertebral cage apparatus within an intervertebral disc space, the method comprising:
    positioning an intervertebral cage apparatus in the intervertebral disc space in a first undeployed position, the intervertebral cage apparatus having a proximal end and a distal end opposite the proximal end along a distal direction, wherein the distal end of the intervertebral cage apparatus comprises a slot; and
    applying a relative force to the distal end along a proximal direction opposite the distal direction with an implantation tool to cause the intervertebral cage apparatus to move from the first undeployed position to a second deployed position, wherein in the second deployed position the proximal and distal ends are closer together along a longitudinal direction that includes the proximal direction and the distal direction than in the first undeployed position, and translation of the proximal end is prevented as the intervertebral cage apparatus moves from the first undeployed position to the second deployed position;
    wherein an outer member of the implantation tool engages the proximal end of the intervertebral cage apparatus, and pins of an inner member of the implantation tool engage the slot of the distal end such that the inner member engages the distal end during the applying step, and the outer and inner members are opposite each other along the longitudinal direction both when the intervertebral cage apparatus is in the first undeployed position and when the intervertebral cage apparatus is in the second deployed position.

2. The method of claim 1, wherein applying a relative force comprises applying a force in the distal direction to the proximal end of the intervertebral cage apparatus while preventing translation of the distal end of the intervertebral cage apparatus.

3. The method of claim 1, wherein the intervertebral cage apparatus comprises a lateral split dividing a portion of the intervertebral cage apparatus into a top portion and a bottom portion.

4. The method of claim 1, wherein the inner member comprises a shaft that extends through an outer cannula, the method comprising rotating the inner member relative to the outer cannula to insert the pins into the slot of the intervertebral cage apparatus.

5. The method of claim 4, further comprising the step of translating the shaft relative to the outer cannula.

6. The method of claim 5, wherein the rotating and translating steps comprise rotating and translating a control member that is attached to the shaft, wherein the control member extends into an aperture in a handle that is attached to the outer cannula.

7. The method of claim 6, wherein rotating the handle causes rotation of the outer cannula.

8. The method of claim 7, wherein a distal end of the outer cannula comprises a connector that defines the outer member of the implantation tool.

9. The method of claim 8, further comprising the step of inserting mating portions of the connector into cutouts at the proximal end of the intervertebral cage apparatus so as to engage the outer member of the implantation tool with the proximal end of the intervertebral cage.

10. The method of claim 1, wherein the outer and inner members are opposite each other along the longitudinal direction both when the intervertebral cage apparatus is in the first undeployed position and when the intervertebral cage apparatus is in the second deployed position.

11. The method of claim 1, wherein the distal end travels along the longitudinal direction toward the proximal end during the applying step.

12. The method of claim 1, wherein the intervertebral cage apparatus comprises a circuitous body that defines the proximal and distal ends.

* * * * *